United States Patent [19]
Housey

[11] Patent Number: 5,877,007
[45] Date of Patent: Mar. 2, 1999

[54] METHOD OF SCREENING FOR PROTEIN INHIBITORS AND ACTIVATORS

[75] Inventor: Gerard Housey, New York, N.Y.

[73] Assignee: ICT Pharmaceuticals, Inc., New York, N.Y.

[21] Appl. No.: 473,169

[22] Filed: Jun. 7, 1995

Related U.S. Application Data

[62] Division of Ser. No. 408,443, Mar. 17, 1995, which is a continuation of Ser. No. 977,986, Nov. 18, 1992, abandoned, which is a continuation of Ser. No. 392,073, Aug. 10, 1989, Pat. No. 5,266,464, which is a continuation-in-part of Ser. No. 154,206, Feb. 10, 1988, Pat. No. 4,980,281.

[51] Int. Cl.$^6$ .............................. C12N 1/21; C12N 1/00; C12P 21/02; G01N 33/573
[52] U.S. Cl. ...................... 435/252.3; 435/7.4; 435/7.71; 435/29; 435/69.1
[58] Field of Search ............................... 435/6, 7.4, 7.71, 435/69.1, 183, 252.3, 29, 240.1, 240.2

[56] References Cited

U.S. PATENT DOCUMENTS

| | | | |
|---|---|---|---|
| 4,980,281 | 12/1990 | Housey | 435/29 |
| 4,981,790 | 1/1991 | Haseltine et al. | 435/69.1 |
| 5,266,464 | 11/1993 | Housey | 435/29 |

*Primary Examiner*—Nancy Degen
*Attorney, Agent, or Firm*—Kenyon & Kenyon

[57] ABSTRACT

Cells useful in the pharmacological characterization of inhibitors or activators of proteins are provided. These cells a protein, the presence of which affects a particular characteristic of the cell which changes in response to substances which inhibit or activate the protein. Such responsive changes in a phenotypic characteristic may be utilized in many useful ways, including the discovery, development or characterization of substances suitable for the treatment of diseases or other conditions in human beings or animals. Such cells may also be useful for studying diseases or other biological processes, for determining the effects of various drugs alone or in combination, as well as for identifying or characterizing substances which may be useful in reducing or preventing the occurrence of a disease or other condition. Through the use of such cells in a cell based assay, tamoxifen is identified as an inhibitor of Protein Kinase C (PKC) activity in cell culture.

1 Claim, 22 Drawing Sheets

FIG. 1.A.-1

```
            10          20          30          40          50          60
             *           *           *           *           *           *
GAA TTC CGC CTC TCC GGG CTT ACA GCC CGC GGT CCC GCC CCG GGG CCG CCA CCT CTC 70          80          90         100         110         120
             *           *           *           *           *           *
GGG GCT CCC CCC AGT CCC CGC GCG CGC AAG ATG GCT GAC CCG GCT GCG GGG CCG CCG
                                    Met Ala Asp Pro Ala Ala Gly Pro Pro 130         140         150         160         170         180
             *           *           *           *           *           *
AGC GAG GGC GAG GAG AGC ACG GTG CGC TTC GCC CGC AAA GGG CCC CTC CGG CAG AAG AAC
Ser Glu Gly Glu Glu Ser Thr Val Arg Phe Ala Arg Lys Gly Pro Leu Arg Gln Lys Asn
```

FIG. 1.A. - 2

```
         190       200       210       220       230       240
          *         *         *         *         *         *
GTG CAC GAG GTG AAG AAC CAC AAA TTC ACC GCC CGC TTC TTC AAG CAG CCC ACC TTC TGC
Val His Glu Val Lys Asn His Lys Phe Thr Ala Arg Phe Phe Lys Gln Pro Thr Phe Cys 250       260       270       280       290       300
          *         *         *         *         *         *
AGC CAC TGC ACC GAC TTC ATT TGG GGC TTC GGG AAG CAG GGA TTC CAG TGT CAA GTC TGC
Ser His Cys Thr Asp Phe Ile Trp Gly Phe Gly Lys Gln Gly Phe Gln Cys Gln Val Cys 310       320       330       340       350       360
          *         *         *         *         *         *
TGC TTT GTT GTA CAC AAG CGC TGC CAT GAA TTC GTC ACG TTC TCC TGC CCT GGT GCA GAC
Cys Phe Val Val His Lys Arg Cys His Glu Phe Val Thr Phe Ser Cys Pro Gly Ala Asp
```

FIG. 1.A. - 3

```
      370       380       390       400       410       420
       *         *         *         *         *         *
AAG GGC CCG GCC TCT GAT GAC CCA CGG AGC AAA CAC AAG TTT AAG ATC CAC ACC TAC TCC
Lys Gly Pro Ala Ser Asp Asp Pro Arg Ser Lys His Lys Phe Lys Ile His Thr Tyr Ser 430       440       450       460       470       480
       *         *         *         *         *         *
AGC CCT ACC TTC TGT GAC CAC TGT GGA TCA CTG CTG TAT GGG CTC ATC CAC CAG GGG ATG
Ser Pro Thr Phe Cys Asp His Cys Gly Ser Leu Leu Tyr Gly Leu Ile His Gln Gly Met 490       500       510       520       530       540
       *         *         *         *         *         *
AAA TGC GAC ACC TGT ATG ATG AAT GTC CAC AAG CGC TGC GTG ATG AAC GTC CCC AGC CTC
Lys Cys Asp Thr Cys Met Met Asn Val His Lys Arg Cys Val Met Asn Val Pro Ser Leu
```

FIG. 1.A. - 4

```
        550       560       570       580       590       600
          *         *         *         *         *         *
TGT GGC ACC GAC CAC ACA GAA CGC CGT GGC CGC ATC TAC ATC CAG GCC CAC ATC GAC AGG
Cys Gly Thr Asp His Thr Glu Arg Arg Gly Arg Ile Tyr Ile Gln Ala His Ile Asp Arg 610       620       630       640       650       660
          *         *         *         *         *         *
GAG GTC CTC ATC GTT GTT GTA AGA GAT GCT AAA AAT CTG GTA CCT ATG GAC CCC AAC GGC
Glu Val Leu Ile Val Val Val Arg Asp Ala Lys Asn Leu Val Pro Met Asp Pro Asn Gly 670       680       690       700       710       720
          *         *         *         *         *         *
TTG TCA GAT CCC TAC GTA AAA CTG ATC CCT GAT CCC AAA AGT GAG AGC AAG CAG
Leu Ser Asp Pro Tyr Val Lys Leu Ile Pro Asp Pro Lys Ser Glu Ser Lys Gln
```

FIG. 1.A. - 5

```
          730         740         750         760         770         780
           *           *           *           *           *           *
AAG ACC AAG ACT ATC AAA TGC TCC CTC AAC CCG GAG TGG AAC GAA ACC TTC AGA TTT CAG
Lys Thr Lys Thr Ile Lys Cys Ser Leu Asn Pro Glu Trp Asn Glu Thr Phe Arg Phe Gln 790         800         810         820         830         840
           *           *           *           *           *           *
CTG AAG GAA TCA GAC AAA GAC AGA AGA CTG TCC GTA GAG ATC TGG GAT TGG GAC CTG ACC
Leu Lys Glu Ser Asp Lys Asp Arg Arg Leu Ser Val Glu Ile Trp Asp Trp Asp Leu Thr 850         860         870         880         890         900
           *           *           *           *           *           *
AGC AGG AAT GAC TTC ATG GGA TCT CTG TCG TTT GGG ATT TCA GAA CTA CAG AAA GCC GGA
Ser Arg Asn Asp Phe Met Gly Ser Leu Ser Phe Gly Ile Ser Glu Leu Gln Lys Ala Gly
```

FIG. 1.A. - 6

```
      910         920         930         940         950         960
        *           *           *           *           *           *
GTG GAT GGC TGG TTC AAG TTA CTA AGC CAG GAA GAA GGC GAG TAC TTT AAT GTG CCG GTG
Val Asp Gly Trp Phe Lys Leu Leu Ser Gln Glu Glu Gly Glu Tyr Phe Asn Val Pro Val 970         980         990        1000        1010        1020
        *           *           *           *           *           *
CCG CCG GAA GAA AGC GAG GGC AAT GAA GAG CTG CGG CAG AAG TTT GAG AGA GCC AAG ATT
Pro Pro Glu Glu Ser Glu Gly Asn Glu Glu Leu Arg Gln Lys Phe Glu Arg Ala Lys Ile 1030        1040        1050        1060        1070        1080
        *           *           *           *           *           *
GGC CAA GGT ACC AAG GCT CCA GAA GAA AAG ACA GCG AAC ACT ATA TCC AAA TTT GAC AAC
Gly Gln Gly Thr Lys Ala Pro Glu Glu Lys Thr Ala Asn Thr Ile Ser Lys Phe Asp Asn
```

FIG. 1.A. - 7

```
          1090        1100        1110        1120        1130        1140
            *           *           *           *           *           *
AAT GGC AAC AGG GAC CGG ATG AAA CTG ACC GAT TTT AAC TTC CTG ATG GTG CTG GGG AAA
Asn Gly Asn Arg Asp Arg Met Lys Leu Thr Asp Phe Asn Phe Leu Met Val Leu Gly Lys 1150        1160        1170        1180        1190        1200
            *           *           *           *           *           *
GGC AGC TTT GGC AAG GTC ATG CTC TCA GAG CGG AAG GGT ACA GAT GAA CTC TAT GCC GTG
Gly Ser Phe Gly Lys Val Met Leu Ser Glu Arg Lys Gly Thr Asp Glu Leu Tyr Ala Val 1210        1220        1230        1240        1250        1260
            *           *           *           *           *           *
AAG ATC CTG AAG AAA GAT GTG GTG ATC CAA GAT GAT GAC GAT GTG GAG TGC ACA ATG GTG GAG
Lys Ile Leu Lys Lys Asp Val Val Ile Gln Asp Asp Asp Val Glu Cys Thr Met Val Glu
```

FIG. 1.A. - 8

```
            1270      1280      1290      1300      1310      1320
              *         *         *         *         *         *
AAG AGG GTG CTG GCC CTG CCT GGG AAG CCC CCA TTC CTG ACT CAG CTC CAT TCC TGC TTC
Lys Arg Val Leu Ala Leu Pro Gly Lys Pro Pro Phe Leu Thr Gln Leu His Ser Cys Phe 1330      1340      1350      1360      1370      1380
              *         *         *         *         *         *
CAG ACC ATG GAC CGC CTC TAC TTT GTG ATG GAG TAT GTG AAC GGG GGC GAC CTC ATG TAC
Gln Thr Met Asp Arg Leu Tyr Phe Val Met Glu Tyr Val Asn Gly Gly Asp Leu Met Tyr 1390      1400      1410      1420      1430      1440
              *         *         *         *         *         *
CAC ATC CAA CAA GTT GGC CGT TTC AAG GAG CCC CAT GCT GTA TTT TAC GCT GCA GAG ATT
His Ile Gln Gln Val Gly Arg Phe Lys Glu Pro His Ala Val Phe Tyr Ala Ala Glu Ile
```

FIG. 1.A. - 9

```
      1450        1460        1470        1480        1490        1500
        *           *           *           *           *           *
GCC ATC GGT CTT TTC TTG CAG AGC AAG GGC ATC ATT TAC CGT GAC CTG AAA CTT GAC
Ala Ile Gly Leu Phe Phe Leu Gln Ser Lys Gly Ile Ile Tyr Arg Asp Leu Lys Leu Asp 1510        1520        1530        1540        1550        1560
        *           *           *           *           *           *
AAC GTG ATG CTG GAT TCC GAG GGG CAC ATC AAA ATC GCT GAC TTT GGC ATG TGT AAA GAG
Asn Val Met Leu Asp Ser Glu Gly His Ile Lys Ile Ala Asp Phe Gly Met Cys Lys Glu 1570        1580        1590        1600        1610        1620
        *           *           *           *           *           *
AAT ATC TGG GAT GGG GTG ACA ACC AAG ACA TTC TGT GGC ACT CCA GAC TAC ATT GCC CCA
Asn Ile Trp Asp Gly Val Thr Thr Lys Thr Phe Cys Gly Thr Pro Asp Tyr Ile Ala Pro
```

FIG. 1.A. - 10

```
           1630      1640      1650      1660      1670      1680
             *         *         *         *         *         *
GAG ATC ATT GCT TAT CAG CCC TAC GGA AAG TCT GTG GAC TGG TGG GCG TTT GGA GTC CTG
Glu Ile Ile Ala Tyr Gln Pro Tyr Gly Lys Ser Val Asp Trp Trp Ala Phe Gly Val Leu 1690      1700      1710      1720      1730      1740
             *         *         *         *         *         *
CTG TAT GAA ATG TTG GCT GGC CAG GCA CCT TTT GAA GGG GAG GAT GAA CTC TTC
Leu Tyr Glu Met Leu Ala Gly Gln Ala Pro Phe Glu Gly Glu Asp Glu Leu Phe 1750      1760      1770      1780      1790      1800
             *         *         *         *         *         *
CAG TCA ATC ATG GAG CAC AAC GTG GCG TAT CCC AAG TCC ATG TCT AAG GAA GCT GTG GCA
Gln Ser Ile Met Glu His Asn Val Ala Tyr Pro Lys Ser Met Ser Lys Glu Ala Val Ala
```

FIG. 1.A. - 11

```
      1810      1820      1830      1840      1850      1860
        *         *         *         *         *         *
ATC TGC AAA GGG CTA ATG ACC AAA CAC CCA GGC AAG CGC CTG GGT TGT GGG CCT GAA GGG
Ile Cys Lys Gly Leu Met Thr Lys His Pro Gly Lys Arg Leu Gly Cys Gly Pro Glu Gly 1870      1880      1890      1900      1910      1920
        *         *         *         *         *         *
GAA CGA GAC ATT AAG GAG CAT GCA TTT TTC CGG TAT ATC GAC TGG GAG AAA CTC GAA CGC
Glu Arg Asp Ile Lys Glu His Ala Phe Phe Arg Tyr Ile Asp Trp Glu Lys Leu Glu Arg 1930      1940      1950      1960      1970      1980
        *         *         *         *         *         *
AAG GAG ATT CAG CCA CCT TAT AAA CCA AAA GCT AGA GAC AAG CGA GAC ACC TCC AAC TTC
Lys Glu Ile Gln Pro Pro Tyr Lys Pro Lys Ala Arg Asp Lys Arg Asp Thr Ser Asn Phe
```

FIG. 1.A. - 12

```
         1990       2000       2010       2020       2030       2040
          *          *          *          *          *          *
GAC AAA GAG TTC ACC AGG CAG CCT GTG GAA CTG ACT CCC ACT GAC AAA CTC TTC ATC ATG
Asp Lys Glu Phe Thr Arg Gln Pro Val Glu Leu Thr Pro Thr Asp Lys Leu Phe Ile Met 2050       2060       2070       2080       2090       2100
          *          *          *          *          *          *
AAC TTG GAC CAA AAT GAA TTT GCT GGC TTC TCG TAT ACT AAC CCA GAG TTT GTC ATT AAT
Asn Leu Asp Gln Asn Glu Phe Ala Gly Phe Ser Tyr Thr Asn Pro Glu Phe Val Ile Asn 2110       2120       2130       2140       2150       2160
          *          *          *          *          *          *
GTG TAG GTG AAT GCA GAT TCC ATC GCT GAG CCT GTG TGT AAG GCT GCA GCG TGA ATG TCT
Val ---
```

FIG. A.1. - 13

```
         2170        2180        2190        2200        2210        2220
          *           *           *           *           *           *
ATT ATC AAT TCC AGT CTT CCA GGA TTC ATG GTG CCT CTG TTG GCA TCC GTC ATG TGG AGA 2230        2240        2250        2260        2270        2280
          *           *           *           *           *           *
GCT TGT CTT AGA GGG CTT TTC TTT GTA TGT ATA GCT TGC TAG TTT GTT TTC TAC ATT TCA 2290        2300        2310        2320        2330        2340
          *           *           *           *           *           *
AAA TGT TTA GTT TAG AAT AAG TGC ATT GCC CAC TGA TAG AGG TAC AAT TTT CCA GAC TTC
```

FIG. 1.A. - 14

```
            2350        2360        2370        2380        2390        2400
              *           *           *           *           *           *
CAG AAA CTC ATC CAA TGA ACC AAC AGT GTC AAA ACT TAA CTG TGT CCG ATA CCA AAA TGC 2410        2420        2430        2440        2450        2460
              *           *           *           *           *           *
TTC AGT ATT TGT AAT TTT TAA AGT CAG ATG CTG ATG TTC CTG GTC AAA GTT TTT ACA GTT 2470        2480        2490        2500        2510        2520
              *           *           *           *           *           *
ACT CTC GAA TAT CTC CTT TGA ATG CTA CCT AAG CAT GAC CGG TAT TTT TAA AAG TTG TGA
```

FIG. 1.A. - 15

```
         *          *          *          *          *          *
        2530       2540       2550       2560       2570       2580
GTA AGC TTT GCA GTT ACT GTG AAC TCT TGT CTC TTG GAG GAA CTT TTT GTT TAA GAA TTG

*          *
        2590       2600
GTA TGA TTA AAC TGA ATT C*
```

METHOD OF SCREENING FOR PROTEIN INHIBITORS AND ACTIVATORS

This application is a divisional application of U.S. Ser. No. 08/408,443, filed 17 Mar. 1995, which is a continuation of U.S. Ser. No. 07/977,986, filed 18 Nov. 1992, now abandoned, which is a continuation of U.S. Ser. No. 07/392,073, filed 10 Aug. 1989, now U.S. Pat. No. 5,266,464, which is a continuation-in-part of U.S. Ser. No. 07/154,206, filed 10 Feb. 1988, now U.S. Pat. No. 4,980,281 the benefit of whose filing date is claimed pursuant to 35 U.S.C. § 120.

BACKGROUND OF THE INVENTION

1. Field of the Invention

This invention relates to a general screening method for the discovery and identification of both inhibitors and activators of enzymes, receptors, and other proteins. In particular, it is concerned with a method of screening for substances which specifically inhibit or activate a particular protein affecting the cultural or morphological characteristics of the cell expressing the protein, especially in a manner apparent to the naked eye.

2. Information Disclosure Statement

A number of assay systems are currently in use for the discovery of new modulators of cell growth, and in particular, in the search for new anti-cancer drugs which are specifically toxic to cancer cells but not to normal cells. A variety of changes may be scored for, but the most common ones are reversion of the transformed phenotype, significant changes in cell morphology, or cytotoxicity. The assays include: (1) in vitro cytotoxicity assays; (2) soft agar colony formation assays; (3) in vitro anti-microbial assays; and (4) assays which detect changes in cellular morphology.

In vitro cytotoxicity assays involve the measurement of cellular parameters which are indicative of inhibition of cellular growth or cytotoxicity. These include, for example, the measurement of the inhibition of certain cellular metabolic pathways in response to treatment with cytotoxic agents. The papers by Von Hoff, et al. (1985), and Catino, et al. (1985) describe typical methods which use this technique. These methods are somewhat complex technically, and require the use of radioactive tracers in some cases. Furthermore, the results are non-specific since any agent which alters the growth properties of cells will score positively in these assay systems.

Agents have also been tested for their ability to inhibit transformed (cancerous) cells from growing in soft agar. This method is based upon the finding by Freedman and Shin (1974) that the formation of colonies of cells in soft agar is the in vitro test which shows the highest correlation in predicting whether the cells will be tumorigenic in an experimental animal. This method is relatively simple to perform since colony growth will, after two or more weeks, generally be large enough to be seen with the naked eye. Scoring the final results, therefore, can be performed either by a technician without extensive training in tissue culture, or, as we describe in the current application, by an automated absorbance detection system. In its present form, however, this method is also non-specific for the same reasons as described above. In other words, any agent which inhibits cellular growth in any way will scores positively in this assay system as it is currently used, whether or not it inhibits the protein of interest.

In vitro anti-microbial assays involve the use of bacterial or yeast strains which are used as test organisms for screening for agents with generalized growth inhibitory properties (also described in Catino, et al., 1985) In this method, the bacterial or yeast strain is grown on standard media plates and potential agents are applied to various spots on the plates. If an agent has growth inhibitory properties, a clear zone results at the site of its application on the plate, resulting from the inability of the test strain to grow in the area. This method is rapid and can be performed by a technician without extensive training in tissue culture techniques, but the results are generally non-specific because agents which are effective against bacterial or yeast strains are frequently less effective (or completely ineffective) in modulating the growth of mammalian cells, as shown in the paper by Catino et al. (1985).

Still other screening systems depend upon a morphologic alteration of the test cells by exposure to the potential agents in order to determine the effectiveness of a given agent. This method is currently the most effective one for developing specific agents which interact with a given protein or alter a specific cellular property, as evidenced by the representative paper by Uehara, et. al. (1985). However, these screening systems are the most difficult ones to apply in practice, since the morphologic effect of each individual agent on the test cells must be studied under the microscope. Hence this method requires extensive observations of the cells by a trained scientist.

SUMMARY OF THE INVENTION

The Method presented in detail in this application combines the rapidity and ease of performance of the soft agar assay with a specificity for detecting an active agent exceeding that of the morphology assay. In brief the method which we describe herein involves the generation of a cell line purposefully engineered to detect both stimulatory and inhibitory agents which are absolutely specific for any given protein which affects the cultural or morphological characteristics of the cell.

The basis for this invention is my observation that if a protein (the "protein of interest", or POI) which is involved in some manner in cellular growth control is overproduced in cells, then pharmacologic agents which can activate or inhibit the POI can result in altered growth properties of the cells.

The sensitivity of the cells is dependent on their production of the POI, a phenomenon referred to herein as a "graded cellular response" to the pharmacologically active agent.

The present invention provides a rapid, yet powerful screening system for the discovery and identification of both inhibitors and activators of proteins. The method may be applied to virtually any type of protein, including enzymes, receptors, DNA- or RNA-binding proteins, or others which are directly or indirectly involved in regulating cellular growth.

The method involves the insertion of a DNA (or cDNA) sequence encoding the Protein Of Interest (POI) into an appropriate vector and the generation of cell lines which contain either (1) the expression vector alone ("control" cell lines) or (2) the expression vector containing the inserted DNA (or cDNA) sequence encoding the POI ("test" cell lines). Using the appropriate vector system, recipient cell lines, and growth conditions, test cell lines can thus be generated which stably overproduce the corresponding POI. Under the appropriate growth conditions, these cell lines will exhibit a "graded cellular response" to activators or inhibitors of the POI. A screening system can thus be set up whereby the control and test cell lines are propagated in defined growth conditions in tissue culture dishes (or even in experimental animals) and large numbers of compounds (or crude substances which may contain active compounds) can be screened for their effects on the POI.

Substances which inhibit or activate the POI may affect characteristics such as growth rate, tumorigenic potential, anti-tumorigenic potential, anti-metastatic potential, cell morphology, antigen expression, and/or anchorage-independent growth capability. Substances which specifically inhibit or inactivate the POI may be distinguished from substances which affect cell morphology or growth by other mechanisms in that they will have a greater effect on the test lines than on the control lines.

The system has been tested using several cDNA sequences and several recipient cell lines, and can be easily automated.

The appended claims are hereby incorporated by reference as an enumeration of the preferred embodiments. All references cited anywhere in this specification are hereby incorporated by reference to the extent pertinent.

BRIEF DESCRIPTION OF THE DRAWINGS

FIG. 1A shows the full-length cDNA sequence, and the deduced amino acid sequence, of one of several forms of PKC which has previously been isolated (cDNA clone RP58), and whose partial sequence has been reported (Housey, et al., 1987). It corresponds to PKCbeta1 according to the nomenclature of Ono, et al. (1987). The deduced amino acid sequence begins with the first in-frame methionine codon at nucleotide position 91 and encodes a 671 amino acid protein with a predicted molecular weight of 76.8 kd. A consensus polyadenylation signal is underlined.

FIG. 1B shows the retrovirus-derived cDNA expression vector, developed in this laboratory, which was used for the present studies. The full-length RP58 cDNA encoding PKC-beta1 (shown in 1A) was cloned into the Eco RI site of plasmid pMV7. The shaded region represents the coding sequence. "E" and "P" designate Eco RI and Pst I restriction sites, respectively. The indicated sizes between restriction sites in the RP58 cDNA are given in kilobases. "LTR" designates the 5' (left) and 3' (right) long terminal repeats of Moloney murine leukemia virus, and "TK-neo" designates the promoter region of the HSV thymidine kinase gene linked to the 5' end of the bacterial neomycin phosphotransferase (neo) gene.

DETAILED DESCRIPTION OF THE INVENTION

Figure 1:
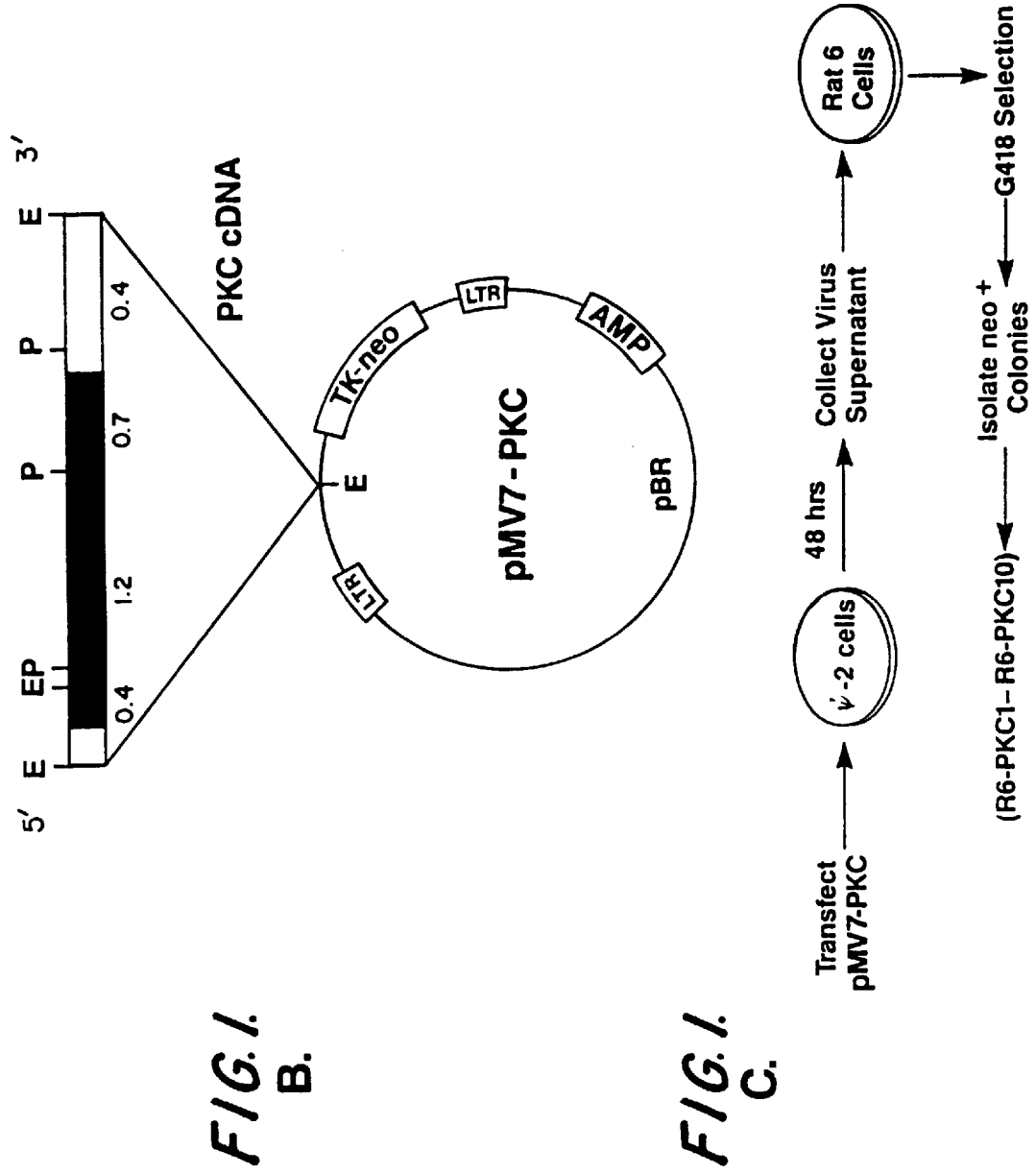
FIG. 1-C outlines in schematic form the overall strategy used to generate cell lines stably overproducing PKC.

The present method is intended for use in identifying potential chemical inhibitors or activators of enzymes, receptors, or any proteins which have effects upon cell phenotype. This method requires two cell lines, preferably alike except for their expression (production) of the protein of interest at different levels (and any further differences necessitated by that difference in expression). Inhibitors or activators are identified by their greater effect on the phenotype of the higher producing cell line.

Any phenotypic characteristic of the cell which is affected by expression of the protein of interest, other, of course, than the level of the protein itself, may be assayed. The phenotypic characteristic is preferably a "cultural" or "morphological" characteristic of the cell. For purposes of the appended claims, these terms are defined as follows:

Cultural characteristics include, but are not limited to the nutrients required for growth, the nutrients which, though not required for growth, markedly promote growth, the physical conditions (temperature, pH, gaseous environment, osmotic state, and anchorage dependence or independence) of the culture which affect growth, and the substances which inhibit growth or even kill the cells.

Morphological characteristics, but are not limited to include the size and shape of cells, their arrangements, cell differentiation, and subcellular structures.

Where the protein of interest is implicated in tumorigenesis or related phenomena, the characteristic observed is preferably one related to cellular growth control, differentiation, de-differentiation, carcinogenic transformation, metastasis, tumorigenesis, or angiogenesis.

Phenotypic changes which are observable with the naked eye are of special interest. Changes in the ability of the cells to grow in an anchorage-independent manner, to grow in soft agar, to form foci in cell culture, and to take up selected stains are particularly appropriate phenomena for observation and comparison.

The higher producing cell line is preferably obtained by introducing a gene encoding the Protein of Interest (POI) into a host cell. The gene may be a one isolated from the genome of an organism, a cDNA prepared from an mRNA transcript isolated from an organism, or a synthetic duplicate of a naturally occurring gene. It may also have a sequence which does not occur exactly in nature, but rather corresponds to a mutation (single or multiple) of a naturally occurring sequence. No limitation is intended on the manner in which this mutated sequence is obtained. The gene is operably linked to a promoter of gene expression which is functional in the host, such that the corresponding Protein Of Interest (POI) is stably "overproduced" in the recipient cells to differing degrees. The promoter may be constitutive or inducible. By "overproduced", I mean that the POI is expressed at higher levels in the genetically manipulated cell line than in the original cell line. This allows one to generate cell lines which contain (or secrete) from as little as a few fold to more than 100-fold elevated levels of the POI relative to the control cells.

Any method may be used to introduce the gene into the host cell, including transfection with a retroviral vector, direct transfection (e.g., mediated by calcium phosphate or DEAE-dextran), and electroporation. Preferably, a retroviral vector is used.

The host cells should exhibit a readily observable phenotypic change as a result of enhanced production of the POI. Preferably, this response should be proportional to the level of production of the POI. Finally, the cells should not spontaneously manifest the desired phenotypic change. For example, 3T3 cells form foci spontaneously. Among the preferred cell lines are Rat-6 fibroblasts, C3H10T 1/2 fibroblasts, and HL60. (HL60 is a human cell line that differentiates in response to PKC activation.) 3T3 cells may be used, but with the reservation stated above.

Generally speaking, it is preferable to maximize the ratio of production by the "overproducing" cell line to production by the "native" line. This is facilitated by selecting a host cell line which produces little or no POI, and introducing multiple gene copies and/or using high signal strength promoters.

The Rat 6 embryo fibroblast cell line is a variant of the rat embryo fibroblast cell line established by Freeman et. al., (1972) and isolated by Hsiao et al., 1986. This cell line has an unusually flat morphology, even when maintained in culture at post-confluence for extended periods of time, displays anchorage dependent growth and, thus far, has not undergone spontaneous transformation. It was also ideal for these studies since it has a very low level of endogenous PKC activity and a low level of high affinity receptors for phorbol esters.

While my most preferred host cell line is the Rat-6 fibroblast cell line, I have tested this Method with other cell types, including the mouse NIH-3T3 cell line as well as the C3H 10T1/2 cell line. Tables (a) and (b) below show the representative specific activities of seven NIH-3T3 and six C3H-10T1/2 cell lines stably overproducing PKC. I have also recently performed the same experiments with the human HeLa cell line. In each case the resulting cell lines all exhibited growth properties qualitatively identical to those described for the PKC-expressing Rat-6 fibroblast cell lines. More specifically, C3H 10T1/2 and NIH 3T3 cells which overproduced PKC exhibited increased cell density, refractility, and rounding relative to the "native" lines. The PKC-overproducing NIH 3T3 cells also displayed increased foci formation. PKC-overproducing C3H 10T1/2 cells also formed foci, but only when exposed to a phorbol ester, i.e., a PKC activator. These results clearly demonstrate that many different types of cells can be employed in this method. The experimental procedures used to generate these cell lines were also identical to those used in connection with the Rat-6 cell line.

If a cell line otherwise suitable for use as a control cell line produces excessive POI, it is possible to inhibit this production by incorporation a known inhibitor into the culture medium for both the control and test cell lines, thus achieving a more favorable ratio of production. Contrawise, if the level of POI production by the test cell line is too low, a known activator may be incorporated into the culture media.

It is desirable, but not necessary, that a suspected inhibitor or activator be tested on both a control line and an overproducing line in parallel.

What we are looking for is a increase in the phenotypic change exhibited by the cell which becomes greater with increasing expression of the POI. We call this a "graded cellular response," and it is by this specialized response that we distinguish inhibitors or activators of the POI from agents that act upon other cell metabolites to effect a phenotypic change.

Thus, in a preferred embodiment, the cell lines are assayed for their relative levels of the POI, and their ability to grow in anchorage-independent systems (e.g., matrices such as soft agar or methocel), to form small "foci" (areas of dense groups of cells clustered together and growing on top of one another) in tissue culture dishes, to take up selected stains, or to bind an appropriately labeled antibody or other receptor for a cell surface epitope. In addition to exhibiting these growth control abnormalities, such cell lines will also be sensitive in their growth properties to chemical agents which are capable of binding to, or modifying the biological effects of, the POI.

The method is particularly unique in that it can be employed to search rapidly for EITHER activators OR inhibitors of a given POI, depending upon the need. The term "activators," as used herein, includes both substances necessary for the POI to become active in the first place, and substance which merely accentuate its activity. The term "inhibitors" includes both substance which reduce the activity of the POI and these which nullify it altogether. When a POI has more than one possible activity. The inhibitor or activator may modulate any or all of its activities.

The use of this screening method to identify inhibitors or activators of enzymes is of special interest. In particular, I am interested in using it to identify inhibitors or activators of enzymes involved in tumorigenesis and related phenomena, for example, protein kinase C, ornithine decarboxylase, cyclic AMP-dependent protein kinase, the protein kinase domains of the insulin and EGF receptors, and the enzyme products of various cellular onc genes such as the c-src ($PP60^{src}$) or c-ras ($P20^{ras}$) genes.

The present invention may be used to identify activators or inhibitors of receptor proteins, both cytoplasmic receptors and integral membrane receptors, provided that overproduction of the receptor protein has a detectable effect on the producing cells.

Protein kinase c (PKC) is a $Ca^{2+}$- and phospholipid-dependent serine/threonine protein kinase of fundamental importance in cellular growth control. PKC is activated endogenously by a wide variety of growth factors, hormones, and neurotransmitters, and has been shown to be a high affinity receptor for the phorbol ester tumor promoters as well as other agents which possess tumor promoting activity (for reviews see Nishizuka 1986; 1984; Ashendel, 1984). PKC has been shown to phosphorylate several intracellular protein substrates, including the epidermal growth factor (EGF) receptor (Hunter et al., 1984), pp60src (Gould et al., 1985), the insulin receptor (Bollag et al., 1986), p21ras (Jeng et al., 1987), and many others (Nishizuka, 1986). Several laboratories have recently isolated cDNA clones encoding distinct forms of PKC, thus demonstrating that PKC is encoded by a multigene family (Ono et al., 1986, Knopf et al., 1986, Parker et al., 1986; Coussens et al., 1986; Makowske et al., 1986; Ohno et al., 1987; Housey et al., 1987). The multiple forms of PKC exhibit considerable tissue specificity (Knopf, et. al., 1986; Brandt et al., 1987; Ohno, et al, 1987; Housey, et. al., 1987) which suggests that there may be subtle differences in the function(s) of each of the distinct forms. However, all of the cDNA clones which have been isolated thus far that encode distinct forms of PKC share at least 65% overall deduced homology at the amino acid level, and transient expression experiments with some of these cDNA clones have shown that they encode serine/threonine protein kinase activities which bind to, or are activated by, the phorbol ester tumor promoters (Knopf, et. al., 1986, Ono, et. al., 1987).

We used the PKCbeta1 cDNA clone for the present studies for the following reasons. With the exception of the brain, where its expression is very high, PKCbeta1 is expressed at very low levels in most tissues, and its expression is virtually undetectable in Rat 6 fibroblasts (see below). Thus, we reasoned that using this form would maximize the phenotypic differences observed between control cells and cells overexpressing the introduced form of PKC. The PKCbeta1 form is also of particular interest because within the PKC gene family its deduced carboxyl terminal domain displays the highest overall homology to the catalytic subunit of the cyclic AMP-dependent protein kinase (PKAc) and the cyclic GMP-dependent protein kinase (PKG) (Housey et al., 1987). The latter observation suggests that PKAc, PKG, and the beta1 form of PKC may share a common ancestral serine/threonine protein kinase progenitor, and that the additional PKC genes may have been derived through evolutionary divergence from the beta1 form.

Agents which interact with certain structural proteins, such as actin and myosin, are also of interest. Mutations in the genes expressing these proteins may be involved in tumorigenesis and metastasization. Such interactions can lead to changes in cell phenotype which can be assayed by this method.

As is set forth in greater detail below, I have produced cell lines which overproduce protein kinase C (PKC). These cell lines, unlike the control cells, grow in soft agar even in the absence of the tumor promoting phorbol ester 12-o-tetradecanoylphorbol-13-acetate (TPA). TPA has been shown to be a potent activator of PKC. When TPA is added to the growth medium the PKC-overproducing cell lines grow even better and form considerably larger colonies in soft agar. Furthermore, I have also tested known inhibitors of PKC activity which, as predicted, caused the PKC-overproducing cells to grow less well (or not at all) in soft agar. Thus, the direct utility of this method in identifying both activators or inhibitors of a gene product, in this case PKC, has been clearly demonstrated.

In additional studies with other genes, most notably the c-H-ras oncogene, the c-myc oncogene, and certain cDNA clones encoding phorbol-ester inducible proteins, overproducing cell lines which exhibited morphological changes relative to the native lines were likewise obtained, and it is believed that such cell lines may be used in screening for inhibitors and activators of the overproduced proteins. Thus it is clear that the method can be generalized to a wide variety of genes encoding proteins which are involved in cellular growth control in numerous cell types. These studies are described in more detail below.

First I tested the capability of pMV7-based expression vectors (pMV7 is my preferred transfer vector) to produce several different types of proteins in various cell lines. I used the cDNA sequences encoding the following proteins: hypoxanthine/guanine phosphoribosyltransferase (HGPRT), the human T4 lymphocyte cell surface antigen, the human T8 lymphocyte cell surface antigen, and ornithine decarboxylase (ODC). In each case the pMV7 vector was capable of producing high levels of expression of the relevant gene thereby resulting in overproduction of the corresponding protein product.

Once I had verified that the pMV7-derived expression vector could reproducibly generate cell lines which stably overproduced proteins I then tested additional genes which encode proteins, other than PKC, which are also involved in cellular growth control.

In further experiments, I have tested the method using an activated c-H-ras oncogene (T24), again in analogous fashion to the techniques described herein, and again with analogous results to those described herein for the PKC cDNA clone. Thus, the Method can also be used for the rapid development of a p21 ras inhibitor. Taken together, the results described in this application demonstrate directly that the Method described herein is clearly generalizable to any gene which is involved in any way in cellular growth control.

In further studies, we have generated additional cell lines which stably overproduce other proteins-of-interest (POIs). In one set of studies, we have introduced the beta1 form of protein kinase C (PKC) into a bone-marrow derived cell line, FDC-P1, and demonstrated that the resulting cell lines are profoundly affected by PKC activators. In a second set of studies, we have developed a screening assay system for insulin agonists and antagonists which utilizes cell lines which stably overproduce the insulin receptor. In these additional studies we have utilized different cell lines, expression vector systems, cDNAs encoding other POIs, and in general varied all of the major parameters of our initial studies in order to demonstrate the true generalizability of the system to any type of cell and any protein-of-interest.

The preferred protein inhibitor/activator drug screening method of the present invention comprises the following steps:
1. Construction of an expression vector which is capable of expressing the protein of interest in the selected host by inserting a gene encoding that protein into a transfer vector. The gene may be inserted 3' of a promoter already borne by the transfer vector, or a gene and a promoter may be inserted sequentially or simultaneously.
2. Introduction of the expression vector (a) into cells which produce recombinant retrovirus particles, or (b)

directly into host cells which will be used for subsequent drug screening tests (the resulting cells are called herein "test" cells).

In parallel, the transfer vector (i.e., the vector lacking the gene of interest and possibly a linked promoter but otherwise identical to the expression vector) is preferably also introduced into the host cells. Cell lines derived from this latter case will be used as negative controls in the subsequent drug screening tests. Alternatively, the unmodified host cells ma) be used as controls.

If 2a was employed, after an appropriate time (usually 48 hours), media containing recombinant virus particles is transferred onto host cells so as to obtain test or control cells.

3. The test and control cells are transferred to selective growth medium containing the appropriate drug which will only allow those cells harboring the expression vector containing the selectable marker gene (as well as the gene or cDNA of experimental interest) to grow. After an appropriate selection time (usually 7–10 days), individual clones of cells (derivative cell lines) are isolated and propagated separately.

4. Each independent cell line is tested for the level of production of the POI. By this method, a range of cell lines is generated which overproduce from a few fold to more that 100-fold levels of the POI. In parallel, the control cell lines which contain only the transfer vector alone (with the selectable marker gene) are also assayed for their endogenous levels of the POI.

5. Each independent line is then tested for its growth capability in soft agar (or methocel, or any other similar matrix) of various percentages and containing different types of growth media until cell lines are identified which possess the desired growth characteristics as compared to the control cell lines.

6. Each cell line is also tested for its ability to form "foci", or areas of dense cellular growth, in tissue culture plates using media containing various percentages and types of serum (20%, 10%, 5% serum, fetal calf serum, calf serum, horse serum, etc.) and under various conditions of growth (e.g. addition of other hormones, growth factors, or other growth supplements to the medium, temperature and humidity variations, etc.). In these tests, the cells are maintained at post-confluence for extended periods of time (from two to eight weeks) with media changes every three days or as required. Such growth parameters are varied until cell lines are identified which possess the desired foci formation capacity relative to the control cell lines under the identical conditions.

7. After a cell line possessing the required growth characteristics is identified, the cells are grown under the conditions determined in (5) above with the growth medium supplemented with either crude or purified substances which may contain biologically active agents specific to the POI. Thus, crude or purified substances possessing the latter properties can be rapidly identified by their ability to differentially alter the growth properties of the experimental cells (which overproduce the POI) relative to the control cells (which do not). This can be done rapidly even by simple observation with the naked eye, since the colonies which grow in soft agar after 2 weeks are easily seen even without staining, although they may be stained for easier detection.

Similarly, if the post-confluence foci formation assay is chosen, the foci which result after approximately two weeks can be easily seen with the naked eye, or these foci can also be stained. For screening very large numbers of compounds (tens of thousands or more), the entire procedure can be performed on 96 well tissue culture plates. This applies equally well for either the soft agar growth assay or the tissue culture foci formation assay. Results of the assays can be rapidly determined by measuring the relative absorbance of the test cells as compared to the control cells (at 500 nm, or another appropriate wavelength). Absorbance readings may be rapidly performed in a 96-well plate absorbance reader such as the "Titer-tek" plate reader, or any of several analogous apparatus currently available. In this fashion, thousands of compounds could be screened per month for their biological activity with very low labor and materials costs.

Furthermore, if antigen expression varies on the test cells expressing high levels of the POI relative to the control cells, a simple Enzyme-Linked Immunoadsorption Assay (ELISA) could be performed and an antibody specific to the antigen.

While the assay may be performed with one control cell line and one test cell line, it is possible to use additional lines, tests lines with differing POI levels. Also additional sets of control/test lines, originating from other hosts, may be tested.

Specific examples implementing the series of steps described above are as follows.

EXAMPLE 1

If one were interested in screening for a protein kinase C (PKC) inhibitor, cell lines would be generated and selected which grow well in soft agar (as a result of their overproduction of any form of PKC) and yet show an enhancement of their growth when compounds which are known to stimulate PKC are added to the growth medium. Appropriate control cells, of course, would not exhibit any of these characteristics. Screening for a potent PKC inhibitor could then be performed by searching for those substances which could selectively inhibit the soft agar (anchorage-independent) growth of the PKC-overproducing cell lines. Alternatively, since the PKC-overproducing cells also form small, dense foci in tissue culture, one could also screen for substances which inhibit this foci formation.

Described below are the detailed aspects of the relevant techniques and methods used to apply the principles of the invention to the problem of developing a system useful for screening for potent inhibitors of protein kinase C (PKC), a high-affinity intracellular receptor for tumor-promoting agents. The cell lines which resulted from the application of this method are highly sensitive and responsive both to agents which activate PKC as well as to those which inhibit PKC.

Construction of plasmid pRV7

The construction of pMV7 was begun with plasmid pPyori which contains the polyoma virus origin of replication cloned into the unique BamHI site of pML-1 (Lusky and Botchan, 1981). This plasmid replicates in murine cells that contain the polyoma T antigen (Dailey and Basilico, 1985). Plasmid pMV (Perkins et al., 1983) was then cleaved with HincII and BglI. The 2.29 kb fragment that contains the Moloney Leukemia Virus Long Terminal Repeats (LTR), the packaging site, the splice donor site, and the proline tRNA binding site was isolated.

During the original construction of pMV (Perkins et al., 1983) 3.95 kb was removed from the MSV genome by cleaving with PstI. This left a PstI site situated 380 bps 3' from the tRNA binding site and 308 bps from the 5' end of the 3' LTR (Reddy et al., 1981). Xho I linkers were added to the HincII-BglI fragment, and to pPyori after it had been cleaved with EcoRI and HindIII. The two fragments were ligated, after activation of the linkers, and a plasmid, designated pMV-3, that contained the Moloney Virus control elements was isolated.

The unique EcoRI site was removed from this vector by digesting the plasmid with EcoRI and treating the linear molecules with T4 polymerase. These molecules were recircularized and a plasmid, pMV-4, lacking the EcoRI site, was isolated. An EcoRI linker was inserted into this plasmid at the PstI site between the Moloney LTRs; the resultant plasmid was designated pMV-5.

The dominant selectable marker (neo) was added to pMV-5. The first step was isolating a 1.9 kb BamHI-SalI fragment from pIPB1. This fragment contains the Herpes Simplex virus thymidine kinase (tk) promoter region and the coding sequence for the bacterial neo gene (neomycin phosphotransferase). This fragment was blunt-ended with T4 polymerase, ClaI linkers were added and the fragment was cloned into the Cla I site 165 bps 3' to the EcoRI site in pMV-5, between the LTRs. This plasmid was designated pMV5-tk neo. The tk promoter has an EcoRI site 70 bps 5' to the start of transcription. This EcoRI site was removed by partially digesting pMV5-tkneo with EcoRI, isolating the linear full length cut species, filling in the ends with T4 polymerase and recircularizing the molecule. A plasmid was chosen in which the EcoRI site previously present in the tk promoter sequence was removed, but the EcoRI site 537 bps 3' to the start of transcription of the 5' LTR was retained. This plasmid was designated pMV7 and a map of this plasmid is shown in FIG. 1B.

This vector consists of the 5' and 3' Moloney Murine Leukemia Virus (MoMuLV) LTRs, the MoMuLV RNA packaging site 3' to the 5' LTR, an Eco RI cloning site, a modified Herpes Simplex Virus thymidine kinase (tk) promoter (lacking an Eco RI site at -79 bp), and the selectable marker gene neo. cDNA clones inserted into the EcoRI cloning site are under the transcriptional control of the 5' LTR, whereas the neo gene is independently transcribed by the tk promoter. This structure favors maintenance of the functional integrity of the selectable marker without interfering with the expression of the 5' (unselected) cDNA sequence. It is known (Maddon et al., 1986; Daley et al., 1987) that when various cDNA sequences are inserted into the EcoR1 site of pMV7 they can be readily transferred into recipient cells by virus-mediated passage, are stably expressed, and yield high-level production of the corresponding protein.

Nucleotide Sequencing and Expression Vector Construction

Nucleotide sequencing of the PKC cDNA clone RP58, a full-length clone isolated from a rat brain cDNA library, which corresponds to the previously reported clone RP41, was performed as previously described (Housey et al., 1987). The full-length cDNA sequence of RP58, which encodes PKCbeta1 (FIG. 1A), was subcloned into the EcoRI site of plasmid pMV7 using standard methodology (Maniatis et al., 1983). The general structure of pMV7 is shown in FIG. 1B. The construct resulting from insertion of the PKCbeta1 gene is designated pMV7-PKCbeta1.

Isolation of cell lines stably overexpressing PKC 20 ug of CsCl banded pMV7 or pMV7-PKCbeta1 plasmid DNA were transfected (Graham and van der Eb, 1973; as modified by Wigler et al., 1977) onto subconfluent "Psi-2" cells (Mann et al., 1985). After 48 hrs the culture medium was collected, filtered through a 0.45 um filter and stored at −70° C. Recipient subconfluent Rat-6 fibroblasts ($5 \times 10^5$ per 10 cm plate) were infected with the virus-containing medium in 2 ug/ml polybrene for 48 hrs. The cells, grown to confluence, were then trypsinized and replaced in Dulbecco's-modified Eagle's medium (DMEM) supplemented with 10% bovine calf serum (CS) (Flow Laboratories) with 200 ug/ml of the neomycin derivative G418 (Geneticin). Resistant colonies were cloned by ring isolation after 1 week of G418 selection.

After approximately ten days of growth in selective medium, ten individual G418-resistant clones were isolated and maintained independently in G418-containing medium. These lines were designated R6-PKCbeta11 through R6-PKCbeta110 (abbreviated as R6-PKC1 through R6-PKC10). In parallel, a set of control Rat 6 lines was generated by transfection of the plasmid pMV7 (lacking the PKC cDNA insert) onto W-2 cells, infection of recipient Rat-6 cells, and selection for G418 resistance as described above for plasmid pMV7-PKCbeta1. Similarly, after ten days of growth in the G418-containing medium, five individual, well-isolated G418-resistant clones were then isolated and maintained independently. These control lines were designated R6-C1 through R6-C5.

RNA Isolation and Blot Hybridization Analyses

Poly A+ RNA isolations, gel electrophoresis, and blot hybridization analyses were performed as previously described (Housey, et. al., 1985). RNA molecular weight markers were obtained from Bethesda Research Laboratories. The 2.7kb cDNA insert of RP58 (see above) was subcloned into plasmid pKS(+) (Stratagene Cloning Systems) to yield a plasmid designated pS2-RP58. A $^{32}$P-labelled probe was prepared from pS2-RP58 and used under high-stringency hybridization conditions as previously described (Housey et al., 1987).

Purification and Assay of PKC Activity From Tissue Culture Cells

The total PKC activity (membrane-associated plus cytosolic) present in cultured cells was determined after partial purification of cellular extracts as follows.

Three 10 cm plates of confluent cells were washed twice with 10 ml of ice-cold phosphate-buffered saline (PBS) and then 10 ml of homogenization buffer (20 mM Tris, pH 7.5, 5 mM EGTA, 5mM EDTA, 15 mM 2-mercaptoethanol, 10 ug/ml soybean trypsin inhibitor, 10 ug/ml leupeptin, 40 ug/ml phenylmethylsulfonyl fluoride), containing 0.1% Triton X-100 were added. The cells were then scraped from each of the plates, pooled and disrupted with 25 strokes in a Dounce homogenizer. The homogenate was transferred to a 15 ml disposable polystyrene tube, centrifuged at 2000×g for 5 minutes at 4° C., and the supernatant was loaded onto a 1 ml DEAE Sephacel column previously equilibrated with 10 ml homogenization buffer, at 4° C. The column was washed with 10 ml homogenization buffer and then the bound enzyme was eluted with 3 ml of homogenization buffer containing 0.5 M NaCl. Total protein concentrations were determined by the method of Bradford (1976).

The PKC activity present in the above-described partially purified cell extracts above was assayed immediately after isolation. The synthetic peptide R—K—R—T—L—R—R—L, corresponding to amino acids 651–658 of the epidermal growth factor receptor (Ullrich et al., 1984), was synthesized on an Applied Biosystems model 430A peptide synthesizer, purified by high-performance liquid chromatography, lyophilized, and stored at −20° C. The Threonine at position 654 is an in vivo substrate for PKC (Hunter, et al., 1984; Davis and Czech, 1985). This synthetic peptide is a highly specific substrate for PKC activity in vitro. (Watson et al., 1987; Woodgett, et al., 1986).

The purified material was then redissolved in sterile water at a final concentration of 100 uM and used as the phosphoacceptor substrate in the PKC assays. The general method of assay has been published in detail elsewhere (O'Brian et al., 1985). In most cases, 100 uM synthetic peptide was substituted for 2 mg/ml histone III-S as the phosphoacceptor substrate.

Cell extracts were prepared 48 hours after the cells had reached confluence. As shown in Table 1(a), eight of the ten cell lines generated by infection with the pMV7-PKCbeta1 construct (lines R6-PKC1, R6-PKC3, and R6-PKC5 through R6-PKC10) contained marked increases in PKC activity when compared to the control lines (R6-C1, -C2, and -C3). It is remarkable that cell line R6-PKC3 contained a 53 fold higher level of PKC activity than that present in the control cells. Two of the lines (R6-PKC2 and R6-PKC4), however, did not display a significant increase in PKC activity, yet they presumably had integrated the pMV7-PKC construct as evidenced by their continued G418 resistance. Subsequent studies verified that these two cell lines contained deletions in the cDNA clone encoding PKCbeta1.

In additional studies I found that the very high PKC activity in extracts of R6-PKC3 seen in the presence of 1 mM $Ca^{2+}$ and phosphatidylserine was also apparent in the presence of 1 mM EGTA, 100 ng/ml TPA and phosphatidylserine. This very high activity was also seen when we employed histone III-S, rather than the above-described synthetic peptide, as the substrate for phosphorylation. Furthermore, even after 24 weeks of continuous growth and serial passage, the cell lines R6-PKC1 through R6-PKC6 displayed essentially the same levels of PKC activity shown in Table 1.

Autophosphorylation and Gel Electrophoresis of PKC

Cell extracts purified as described above were incubated under conditions which favor the autophosphorylation of PKC, as follows. One hundred ug of partially purified protein extract was incubated in a reaction mixture containing 80 ug/ml phosphatidylserine, 1 mM $CaCl_2$ (or 1 mM EGTA and 100 ng/ml TPA), 5 mM $MgCl_2$, and 30 uM ATP containing 100 uCi [gamma-$^{32}$P]ATP (New England Nuclear, NEG035). The purity of the radioactive ATP is critical to obtain reproducible autophosphorylation of PKC.

Under these conditions, it has been previously shown that PKC undergoes an autophosphorylation reaction which results in the phosphorylation of several sites on the intact enzyme (Walton et al., 1987; Huang et al., 1986, Woodgett and Hunter, 1986; Kikkawa, 1982).

Reactions were incubated at room temperature for 10 minutes and then stopped by the addition of SDS-PAGE loading buffer containing 2-mercaptoethanol. This material was then subjected to discontinuous SDS-PAGE by a modification of the method of Laemmli (1970). Twenty ug of total protein were loaded onto each lane. Following electrophoresis, the gels were fixed in 50% acetic acid, 10% ethanol, dried, and autoradiographed on Kodak XAR-5 film.

Figure 2:
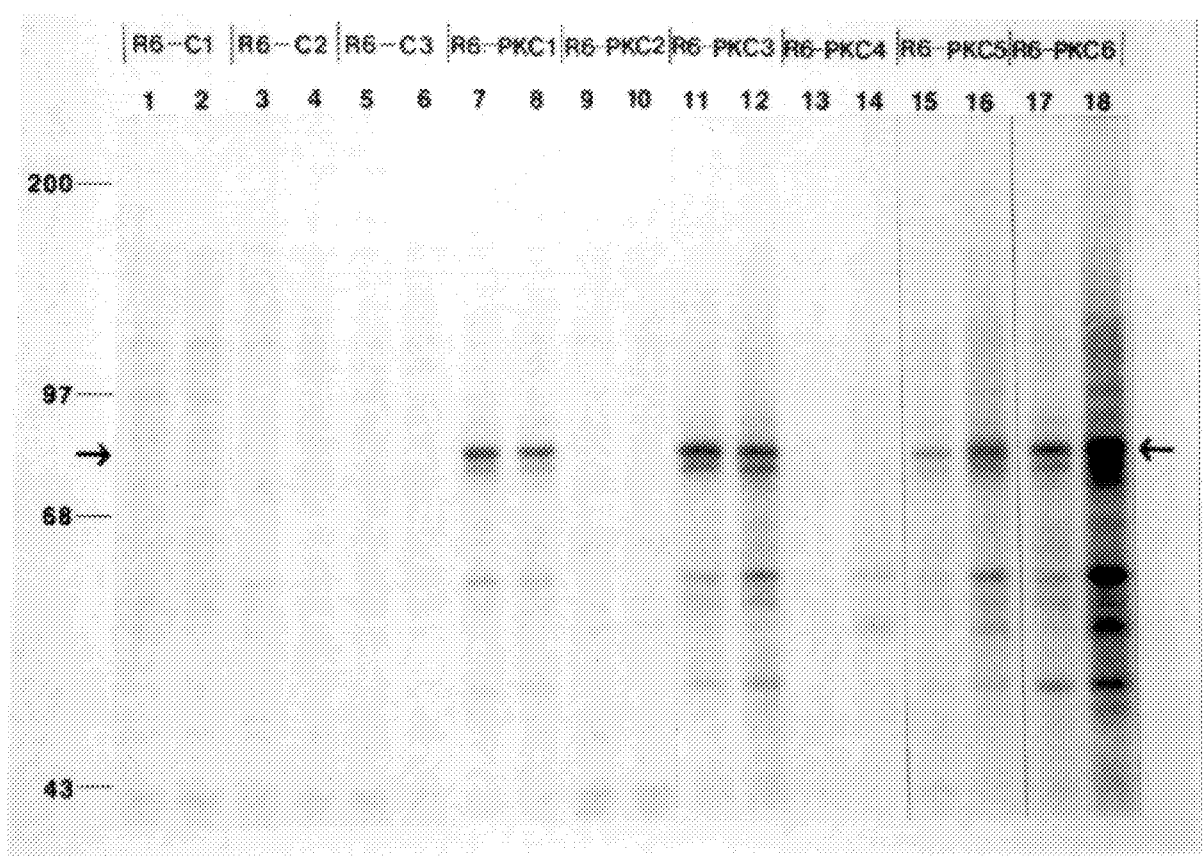
FIG. 2. Purification and Autophosphorylation of PKC. PKC activity from each cell line was purified and subjected to reaction conditions favoring autophosphorylation of PKC. Following the autophosphorylation reaction, protein samples were separated by discontinuous polyacrylamide gel electrophoresis. In the lanes bearing odd numbers the reaction mixtures contained 1 mM Ca2+ and phosphatidylserine to activate PKC, and in the lanes bearing even numbers the reaction mixtures contained 1 mM EGTA, 100 ng/ml TPA, and phosphatidylserine. The numbers in the left margin indicate the sizes of molecular weight markers, in kd. Arrows indicate the position of the 75 kd autophosphorylated PKC.

Autoradiographs of these gels (FIG. 2) revealed that the extracts prepared from four cell lines that had high PKC activity (R6-PKC1, -PKC3, -PKC5, and -PKC6, see Table 1(a)) displayed a prominent phosphorylated protein band which was about 75 kd in size, corresponding to the size of an autophosphorylated preparation of PKC obtained from rat brain (Huang et al., 1986; Housey et al., 1987). When examined in an immunoblot assay this 75 kd band also reacted with an antibody to the beta1 form of PKC (Jaken and Kiley, 1987). The control cell lines R6-C1, -C2 and -C3, and the cell lines R6-PKC2 and R6-PKC4, which did not have increased levels of PKC (see Table 1(a)) did not show this 75 kd phosphorylated band (FIG. 2), nor did they contain any bands which reacted with the antibody to the beta1 form of PKC. It is of interest that the samples obtained from the four cell lines that produced high levels of PKC also displayed weaker but distinct phosphorylated protein bands that were about 73, 60, and 49 kd in size, which were not seen (or only faintly detected) in the extracts from cells that did not have increased levels of PKC (FIG. 2). These bands may represent degradation fragments of the 75 kd PKC molecules, or specific cellular proteins that are phosphorylated by PKC.

The above-described phosphorylated protein bands were seen when either 1 mM Ca2+ plus phosphatidylserine or 100 ng/ml TPA plus phosphatidylserine were used as cofactors for PKC activation (compare even and odd numbered lanes in FIG. 2). When, however, extracts from cell lines producing high levels of PKC were incubated in an autophosphorylation reaction in the absence of such cofactors, the 75 kd band and the additional smaller bands described above were not detected. These results, taken together with the negative results obtained with extracts from the control cells (FIG. 2), clearly indicate that the phosphorylated bands reflect PKC activity.

Phorbol Ester ($^3$H-PDBU) Binding Assays

Since it has been shown that PKC is a high affinity intracellular receptor for the phorbol ester tumor promoters (for review, see Nishizuka, 1986), I also assayed a subset of the cell lines for 3H-PDBu binding using a previously described intact cell assay (Horowitz et al., 1981).

Cells were plated at $1 \times 10^5$ per 4 cm well on day 1, the medium was changed on day 2 and the cells then assayed on day 3. The monolayer was washed with 4 ml of DMEM (without serum), then 2 ml of DMEM containing 50 nM $^3$H-PDBU (New England Nuclear; 8.3 Ci/mmol) was added and the plates were incubated for 1 hr at 37° C. to determine total binding. The fraction of the total binding that represented specific binding was determined by the addition of a 1000-fold excess of unlabelled PDBU (LC Services) to the 3H-PDBU stock (Horowitz et al., 1981). The plates were washed 3× with 4 ml ice-cold PBS. The cells were solubilized in 1 ml 1% SDS/10 mM DTT for 2 hrs at 37° C. The lysate was transferred to a scintillation vial and counted. Replica plates were used to determine the number of cells per plate and the specific binding data expressed as nanomoles 3H-PDBu bound/$10^6$ cells. Scatchard analyses were performed as previously described (Horowitz et al., 1981).

I found that the R6-PKC cell lines 1,3,5 and 6, all of which had high PKC enzyme activity, also had a marked increase in 3H-PDBu binding, whereas the cell line R6-PKC4, which did not display a significant increase in PKC activity, did not show an increase in 3H-PDBu binding when compared to the two control cell lines R6-C1 and R6-C2 (Table 1(a)). Scatchard analyses of the control cell line R6-C1 and of the R6-PKC3 cell line, performed as previously described (Horowitz et al., 1981), indicated that the number of high affinity receptors in the two cell lines was $1.6 \times 10^5$ and $1.4 \times 10^6$, respectively. The affinity constants were approximately the same in both cell lines (Kd=16 nM). Thus, under the assay conditions used, the R6-PKC3 cells contain about ten times the level of high affinity phorbol-ester binding sites as the control cells. It is apparent that the cell lines that express very high levels of PKC also have a significant increase in phorbol ester binding sites.

Assays for PKC-related RNA transcripts

In view of the above results, it was of interest to analyze the poly A+ RNA fraction of several of the cell lines described in Table 1(a) for the size and abundance of RNA transcripts containing sequences homologous to PKCbeta1.

Figure 3:
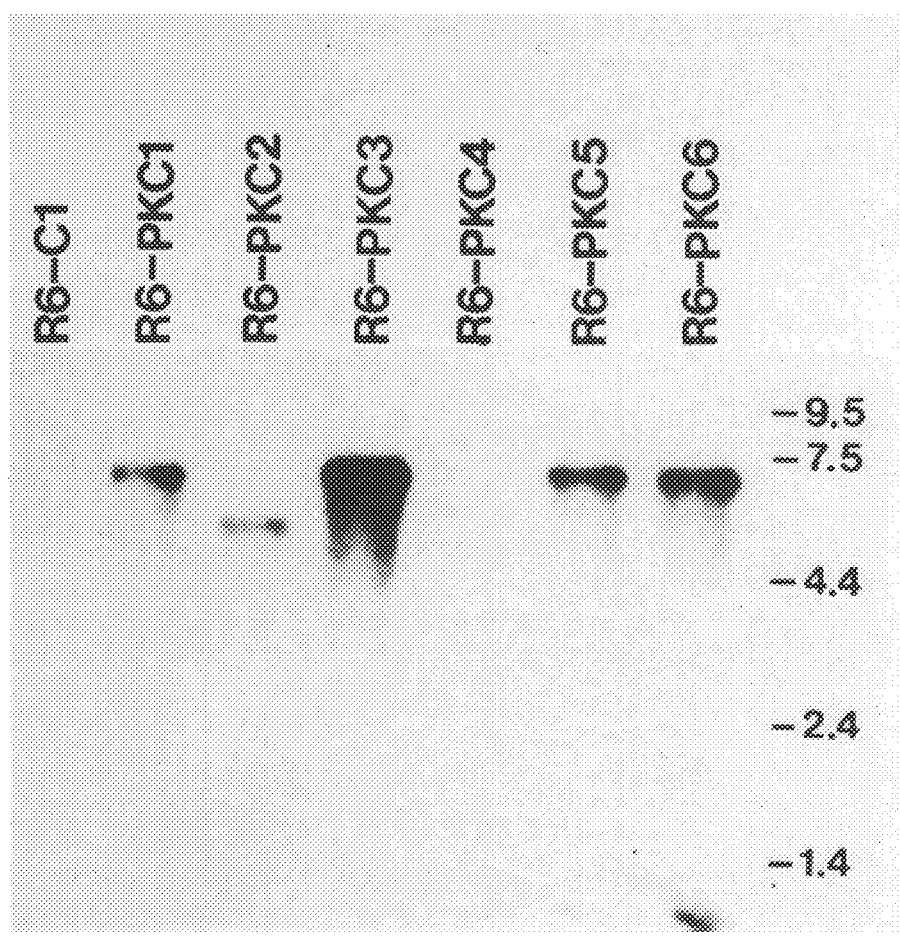
FIG. 3. Northern Blot Hybridization Analyses. Poly A+ RNA was isolated from the indicated cell lines and separated by electrophoresis on 6% formaldehyde/1% agarose gels, blotted onto nylon membrane and hybridized with the 32P-labelled full-length RP58 cDNA probe, as previously described (Housey, et. al., 1987). The numbers in right margin indicate the sizes in kb of the RNA markers. The R6-PKC4 sample displayed a very weak 4.8 kb band on the original autoradiograph.

Poly A+ RNA was separated on 1% agarose, 6%-formaldehyde gels, blotted onto nylon membranes, hybridized to a 32P-labelled DNA probe prepared from the full-length PKCbeta1 cDNA, and autoradiographed, as previously described (Housey, et al., 1986). As shown in FIG. 3, the lines that contained elevated levels of PKC activity (R6-PKC1,-PKC3,-PKC5, and -PKC6, see Table 1(a)) contained a prominent 6.6 kb RNA species which corresponds to the predicted size for a mRNA transcript that initiates in the 5' LTR and terminates in the 3' LTR of the pMV7-PKCbeta1 construct. This transcript was most abundant in the R6-PKC3 cell line (FIG. 3) which also expresses the highest level of PKC activity (Table 1).

On the other hand, lines R6-PKC2 and R6-PKC4, which showed no significant elevation of PKC activity (Table 1(a)), produced truncated mRNA's of approximately 5 kb and 4.8 kb, respectively. The abundance of the latter transcripts was much lower than that of the 6.6 kb transcripts present in the cell lines that expressed high levels of PKC. The neo+ phenotype and the lack of PKC activity in cell lines R6-PKC2 and R6-PKC4 suggest that the truncated mRNAs reflect deletions in PKC coding sequences in the integrated constructs carried by these cell lines. Indeed, genomic DNA blot hybridizations of clones R6-PKC2 and R6-PKC4 indicated that they contained deletions in the PKCbeta1 cDNA sequence. Neither in the parental Rat 6 cell line, nor in any of the experimental cell lines derived from these cells, was it possible to detect evidence of an endogenous transcript homologous to the PKCbeta1 probe (FIG. 3). Thus, in these cells, there is negligible expression of the endogenous gene encoding PKCbeta1.

Assays of Growth in Monolayer Culture and in Soft Agar

Cells were seeded at a density of $10^4$/plate in a series of 60 mm plates, in 5 ml DMEM plus 10% CS. Twenty-four hours later, cells in triplicate plates were trypsinized and counted. This point was designated "day 0." The remaining cultures were then grown in the respective medium (i.e. plus or minus 100 ng/ml TPA) with fresh medium changes twice per week. Cell counts per plate were then determined on triplicate plates during the remainder of the growth curve (FIG. 3). The results obtained were analyzed for exponential doubling time and saturation density (Table 2). To assess growth in soft agar (anchorage independence), $2\times10^4$ cells were suspended in 2 ml of 0.3% Bacto agar (Difco Laboratories, Detroit, Mich.) In DMEM containing 20% fetal calf serum (FCS) and overlayed above a layer of 5 ml of 0.5% agar in the same medium, on 60 mm petri dishes. The cells were then overlaid with DMEM plus 20% FCS every 4 days. At the end of 30 days, colonies were stained with the vital stain 2-(p-iodophenyl)-3-(p-nitrophenyl)-5-phenyltetrazolinium chloride hydrate (INT) (Sigma Chemical Co., St. Louis, Mo.) for 48 hours at 37° C., in an incubator with 5% C02 (Schaeffer and Friend, 1976), and the number of colonies counted under low power on an inverted phase microscope. The data are expressed as "cloning efficiency", i.e. number of colonies greater than 0.05 mm per plate X 100 divided by the number of cells originally seeded per plate.

Screening of a Known Activator of PKC

We found that cell lines which overproduce PKC display an exaggerated morphologic response to 12-0-tetradecanoyl phorbol-13-acetate (TPA) and altered growth control.

Changes in Morphology

Figure 4:
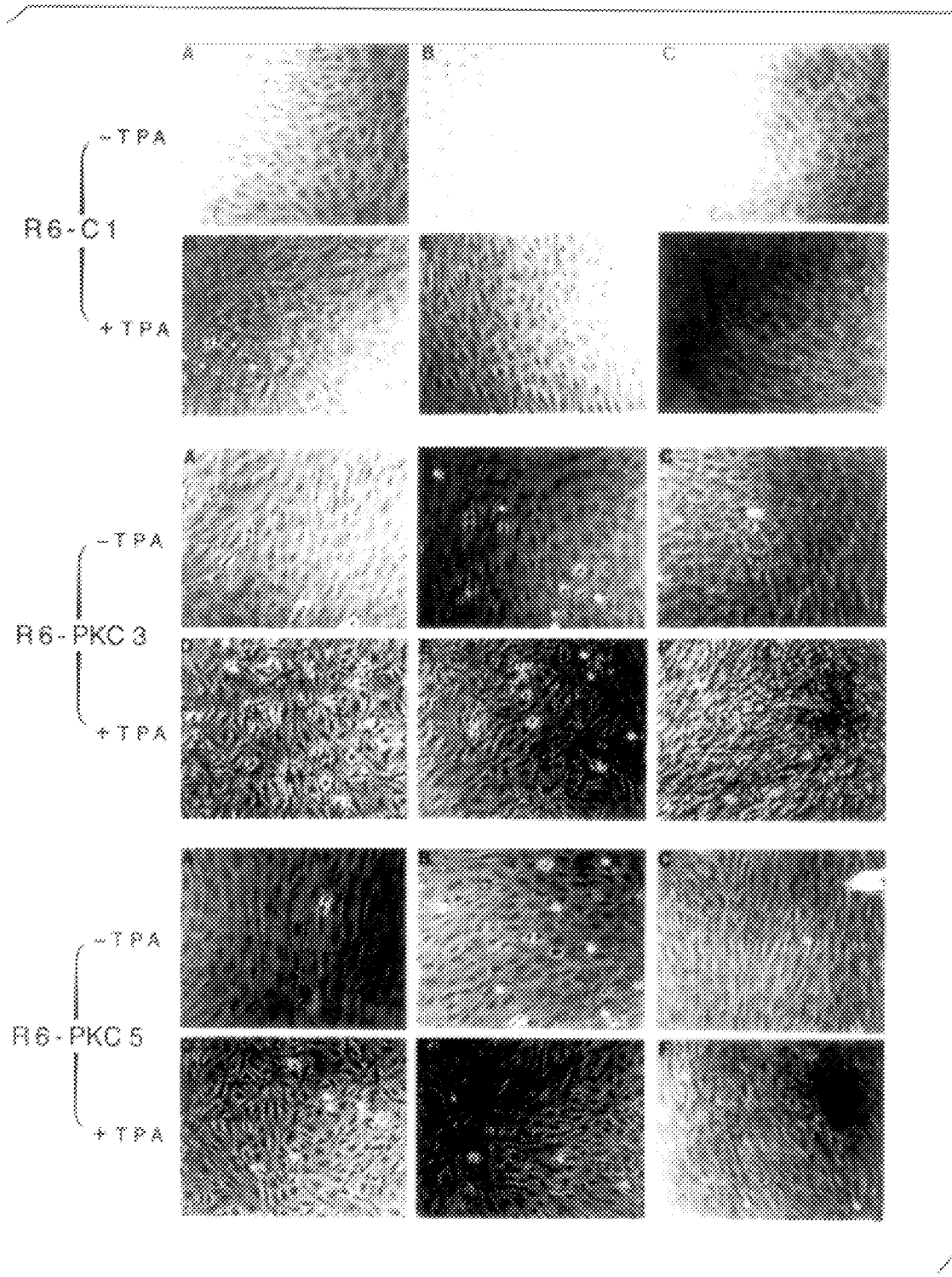
FIG. 4. Morphologic Responses of the Cell Lines to Phorbol Ester Treatment. Nearly confluent cultures of the three indicated cell lines were exposed to 100 ng/ml TPA in 0.1 % dimethylsulfoxide (DMSO) solvent ("+TPA") or 0.1% DMSO alone ("−TPA"), in DMEM plus 10% CS. Photographs were taken 24 hours later (Panels A and D) and 48 hours later (Panels B and E). Fresh medium plus or minus TPA was then added and photographs were then taken an additional 24 hours later (Panels C and F). (Magnification: 100×).

To further characterize the phenotypic changes which occurred in the cell lines that overproduce PKCbeta1, lines R6-PKC3 and R6-PKC5, which contain 53- and 20-fold elevations of PKC activity, respectively, were first examined in detail with respect to their morphology, in comparison to the control cell line R6-C1. As shown in FIG. 4, Panel A, in the absence of TPA treatment all three cell lines showed the characteristic fusiform morphology of monolayer cultures of the normal parental Rat 6 fibroblast cell line. At 24 hours after treatment with 100 ng/ml TPA (FIG. 4, R6-C1: panel D), the control cell line displayed more elongated and dendritic cells and a criss-cross pattern, changes previously seen shortly after rodent fibroblasts are treated with TPA (Boreiko et al., 1980). These changes were, however, much more dramatic when the R6-PKC3 and R6-PKC5 cells were treated with TPA (R6-PKC3 and R6-PKC5, Panel D). This was particularly striking with the R6-PKC3 cells (which express the highest level of PKC) since they displayed very long cytoplasmic processes and numerous retractile cell bodies.

By 48 hours following exposure to TPA the morphology of the control cell line R6-C1 had returned to its normal appearance (FIG. 4, Panel E). On the other hand, the R6-PKC3 cells, and to a lesser extent the R6-PKC5 cells, continued to display an altered morphology. All of the cell lines were then exposed to a second, fresh dose of TPA (100 ng/ml) and examined 24 hours later (FIG. 4, Panel F), i.e., 72 hours after the first dose of TPA. The control cells failed to respond, in terms of morphologic change, to the second dose of TPA whereas the R6-PKC3 cells continued to display their altered morphology as well as an increase in cell density. The R6-PKC5 cells displayed only slight changes in morphology in response to the second dose of TPA.

Presumably, the very high level of constitutive production of PKC in the R6-PKC3 cell line is responsible for their exaggerated morphologic response to TPA as well as the failure of these cells to display the usual refractory response to TPA following an initial exposure. In normal cells, the latter response appears to be due to "down-regulation" of endogenous PKC activity. Since the R6-PKC5 cells have an intermediate level of PKC, it is not surprising that their morphologic responses to TPA are intermediate between those of the control cells and the R6-PKC3 cells.

Growth Curves

It was also of interest to determine the growth rates of these cells in monolayer culture. Detailed growth curves were performed on R6-C1, R6-PKC3 and R6-PKC5 cells in 10% calf serum and DMEM medium, in the absence and presence of 100 ng/ml TPA. The data obtained are summarized quantitatively in Table 2.

In the absence of TPA, the R6-C1 control cell line displayed the longest doubling time (26.4 hours) and the lowest saturation density ($3.4\times10^6$ cells/plate); the R6-5 cell line had a shorter doubling time (24.9 hours) and a higher saturation density ($4.8\times10^6$ cells/plate); and the R6-PKC3 cell line had the shortest doubling time (24.2 hours) and the highest saturation density ($5.7\times10^6$ cells/plate). The presence of TPA decreased the doubling times, and also increased the saturation densities of all three cell lines, but the enhancement by TPA was particularly striking in the case of R6-PKC3 (Table 2).

When the cell lines were maintained in the presence of TPA for a longer period of time, the R6-PKC3 cells, but not the R6PKC5 or R6-C1 cells, showed a decline in cell density. The latter effect was due to the fact that when the R6-PKC3 cells were maintained at high cell density in the presence of TPA they became less adhesive and tended to detach from the plate.

Thus, even in the absence of TPA the R6-PKC3 cells, (which have the highest level of PKC), and to a lesser extent the R6-PKC5 cells (which have an intermediate level of PKC), exhibit an enhancement of their growth properties which is even greater than that seen when the R6-C1 control cells are grown in the presence of TPA. Moreover, in the presence of TPA these differences in growth properties between the control and R6-PKC3 cells are even more striking.

Foci Formation

Figure 5:
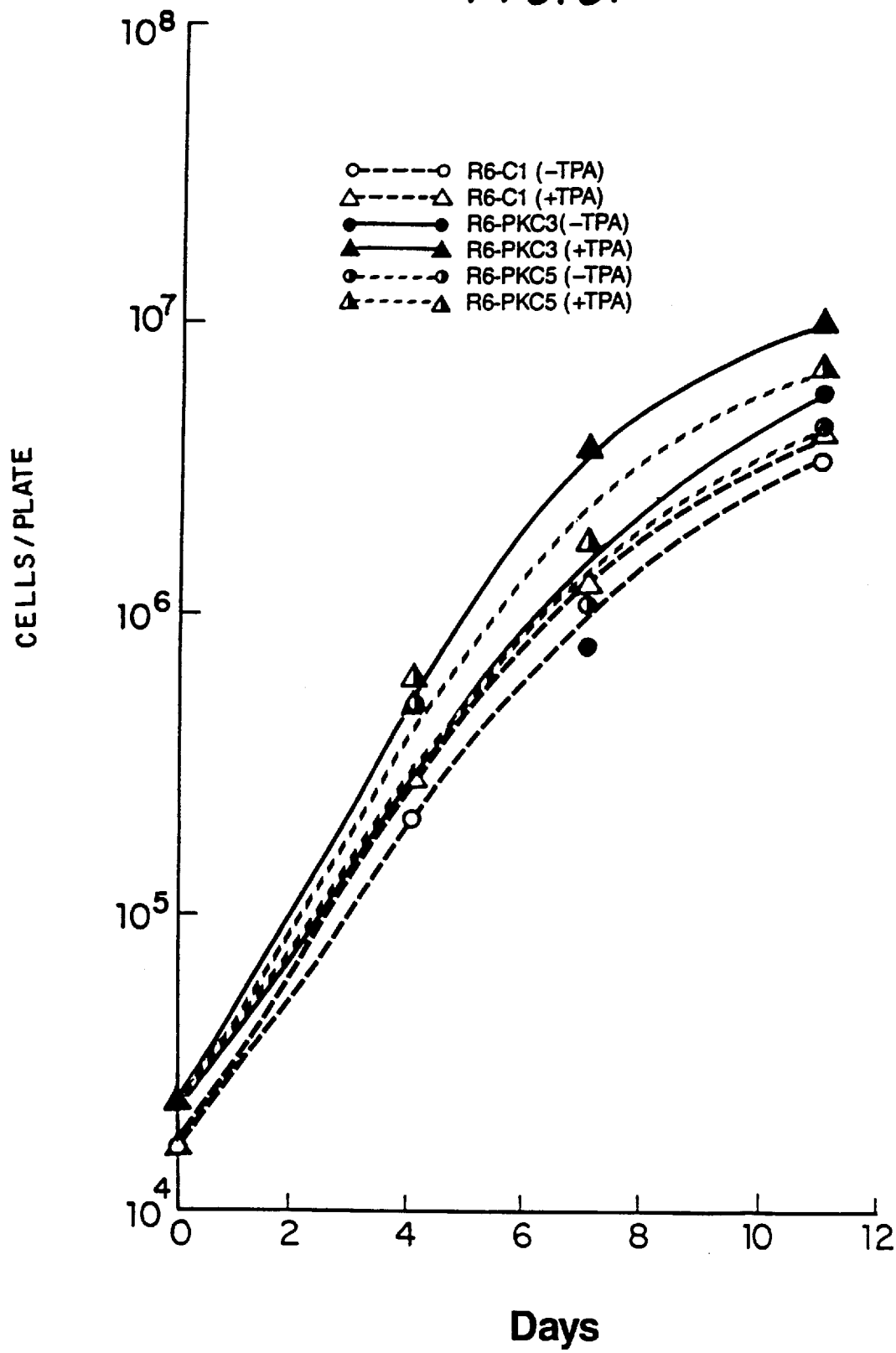
FIG. 5. Growth Curves of Control and PKC-Overproducing Cell Lines. The indicated cell lines were seeded at $1 \times 10^4$ per 6 cm plate in DMEM plus 10% CS, in the presence ("+TPA") and absence ("−TPA") of 100 ng/ml TPA. Cell numbers were determined in replicate plates during the subsequent 11 day growth period. The values given indicate the means of triplicate determinations, which varied by less than 10%.

In additional studies, monolayer cultures were maintained at post-confluence for an extended period of time (28 days), with media changes every 3 days, in the absence of TPA. Whereas the control R6-C2 cell line remained a fairly uniform monolayer, after about 21 days the R6-PKC3 cell line developed numerous dense foci which were approximately 0.1–0.3 mm in diameter (FIG. 5). Furthermore, the R6-PKC3 cultures displayed numerous cells with a highly vacuolated cytoplasm which were scattered throughout the monolayer, but were not seen in the R6-C2 control culture. When the dense foci seen in the R6-PKC3 culture were picked and further passaged they grew like the parental R6-PKC3 cells and did not display a morphology typical of malignantly transformed cells. It may be surmised that these dense foci, and the vacuolated cells, reflect physiologic rather than genetic changes induced by the high level of PKC activity.

Growth on Soft Agar

Figure 6:
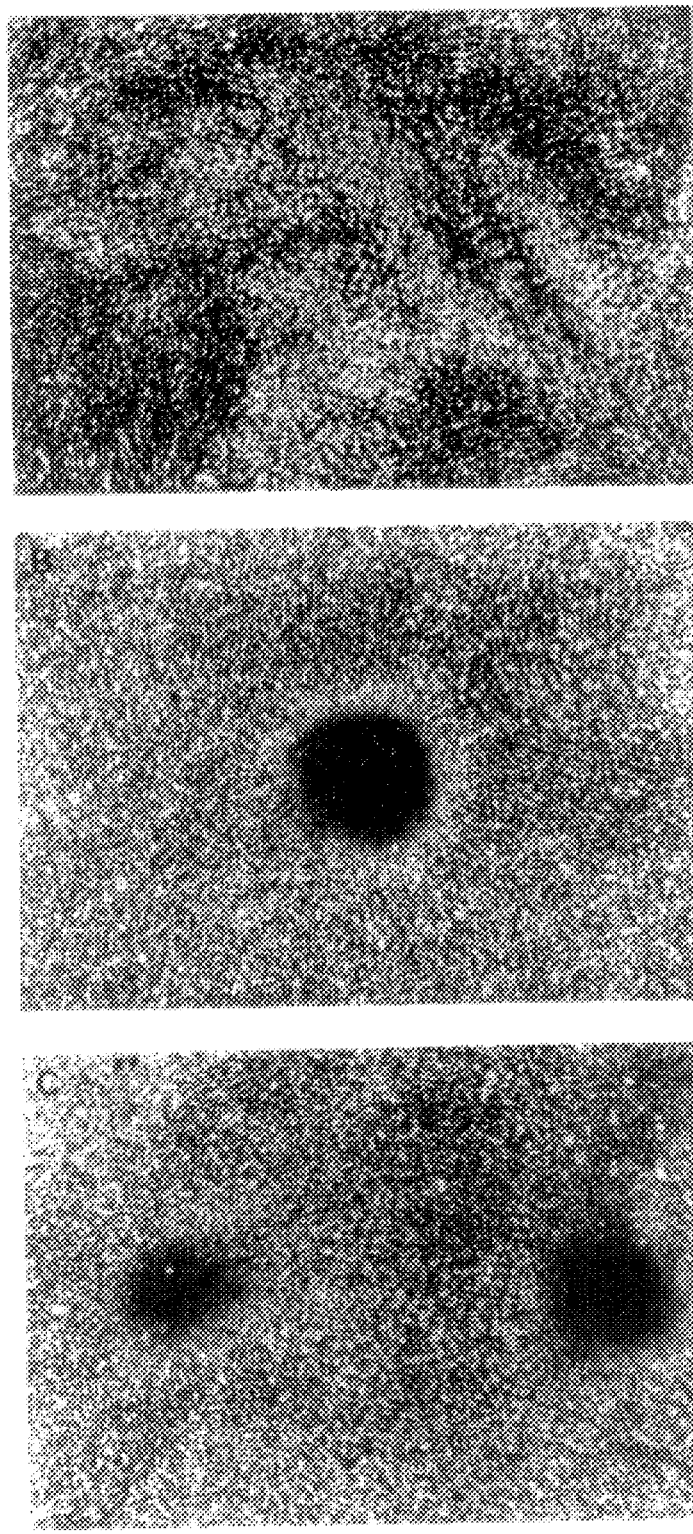
FIG. 6. Post-confluence Foci Formation. Control R6-C2 cells (Panel A) and R6-PKC3 cells (Panels B and C) were grown to confluence and then maintained for an additional 28 days in DMEM plus 10% CS (without TPA), with the addition of fresh medium every 3 days. Photographs were taken at the end of the 28 day period. Magnification: 40×.
Figure 7:
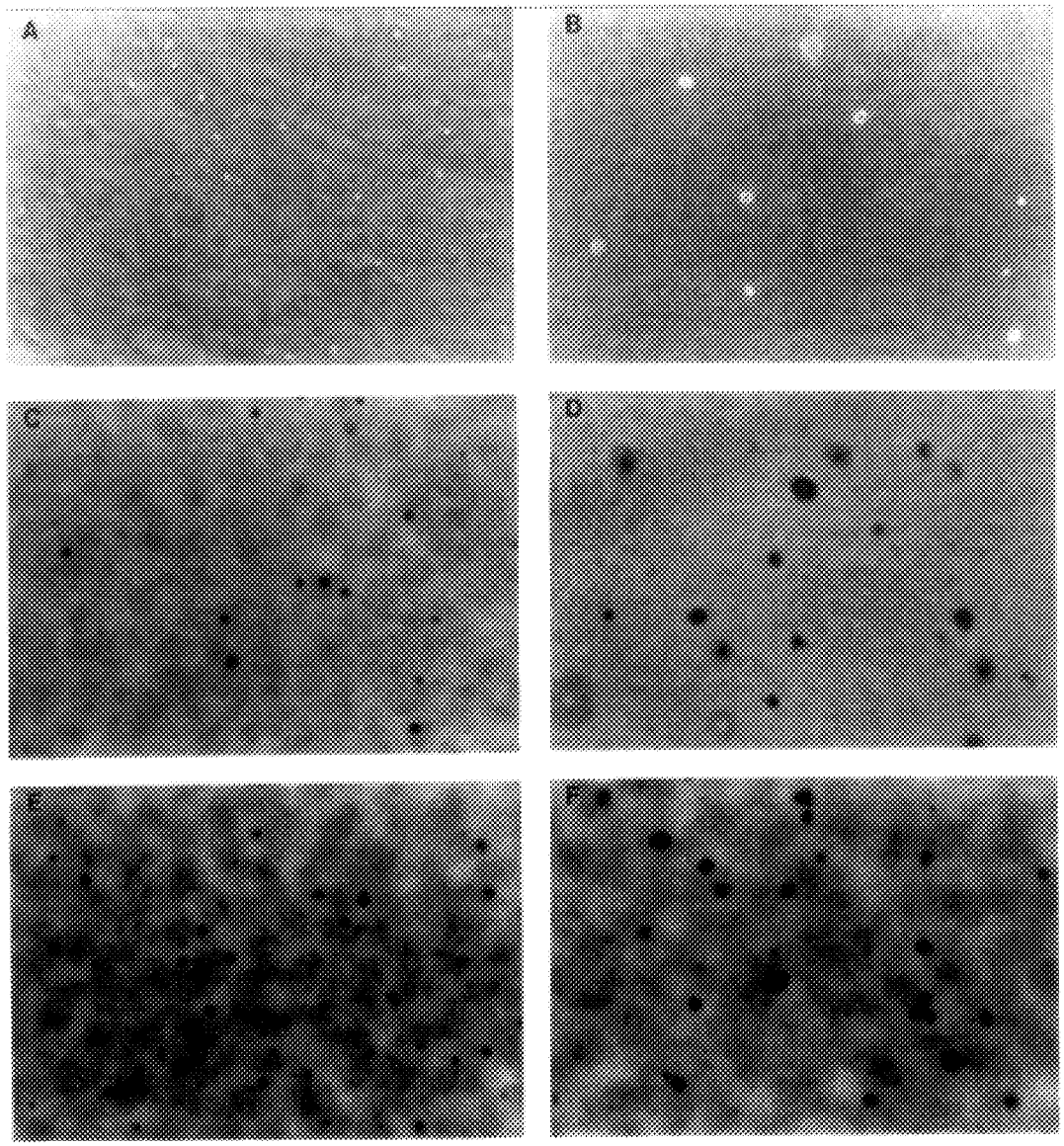
FIG. 7. Growth in Soft Agar. Cell lines R6-C1, R6-PKC3, and R6-PKC5 were seeded into 60 mm petri dishes in 0.3% agar containing DMEM plus 20% FBS and 50 lg/ml G418, plus or minus 100 ng/ml TPA. Photographs were taken after 21 days of growth. A) R6-C1+TPA (low-power field) B) R6-C1+TPA (medium-power field) C) R6-PKC3 D) R6-PKC3+TPA E) R6-PKC5 F) R6-PKC5+TPA. For additional details see Experimental Procedures. (Magnification: 100× in panel B; 40× in all other panels).

I also assayed these cell lines for their ability to form colonies in soft agar, since with rodent cells the acquisition of anchorage-independent growth often correlates with tumorigenicity (Freedman and Shin, 1974). As shown in FIG. 6, when $2 \times 10^4$ cells were plated in 0.3% soft agar, both the R6-PKC3 and the R6-PKC5 cells formed numerous small colonies, whereas the control R6-C1 cells (and the parental Rat 6 cell line) failed to grow and persisted as single cells. In addition, when TPA (100 ng/ml) was added to the agar medium, the colony sizes and cloning efficiencies of the R6-PKC3 and RC-PKC5 cells were enhanced (FIG. 6 and Table 2), but the R6-C1 cells still failed to grow in agar.

The cloning efficiencies and colony sizes of the R6-PKC3 cultures were always greater than those of the R6-PKC5 cultures, both in the absence and presence of TPA (Table 2), presumably reflecting the higher level of PKC activity in the former cell line. Thus, it is clear that the overproduction of PKC is associated with the acquisition of anchorage-independent growth in Rat 6 cells. The sizes of the colonies formed in agar by the PKC cell lines are smaller than those formed by Rat 6 cells transformed by an activated c-H-ras oncogene, which have a diameter of about 0.5–1.0 mm.

Further Screening of Activators and Inhibitors of PKC

Additional compounds tested included the tumor promoters teleocidin, aplysiatoxin, and mezerein, all of which are known activators of PKC (O'Brian, et al., CSH, 1985). Furthermore, a known inhibitor of PKC, H-7 (Kawamoto and Hidaka, 1984), also modulated the growth of the cells in the expected manner.

Moreover, this method has been used to establish that the anti-estrogen tamoxifen (O'Brian, et al, Cancer Res., 1985), which inhibits PKC enzyme activity in a cell-free assay, is capable of completely inhibiting the growth in agar of all of the cell lines overproducing PKC. Inhibition of the growth of the R6-PKC3 cells in agar in the presence of tamoxifen provided critical evidence that tamoxifen could inhibit PKC-mediated stimulation of cellular growth.

Furthermore, the concentration of the inhibitor necessary to completely inhibit the growth of each cell line was roughly proportional to the amount of PKC being overproduced in that particular cell line. In other words, there is a direct relationship between the molar amount of inhibitor required to prevent cell growth and the molar amount of PKC present in each cell line.

In addition, I have demonstrated the analogous relationship between the molar amounts of PKC activators and the molar amounts of PKC present in cells. In other words, there is a direct relationship between the molar amount of activator required to stimulate cell growth and the molar amount of PKC present in cells. Thus, this work establishes, for the first time, the fact that stable overproduction of a protein in mammalian cells can result in a novel cellular phenotype(s) (in this case anchorage independence) which can be directly modulated by chemical agents which interact with the protein.

EXAMPLE 2

If one were interested in screening for a potent inhibitor of the c-H-ras oncogene product (the p21 protein) then one would generate cells which grow well in soft agar with appropriate media conditions when p21 is stably overproduced at a certain level, but not at all when p21 is present at wild type levels. Screening for a potent p21 inhibitor could then be performed as described in Example 1 above.

EXAMPLE 3

The same basic techniques would also apply to genes (or cDNA sequences) which have been mutated either by laboratory design (e.g. site-directed mutagenesis) or as a result of naturally occurring events. Thus, any of the known point mutations in the ras oncogene which result in greater capability by the mutated gene to transform normal cells to cancerous ones could be employed in the same basic procedures as described above.

EXAMPLE 4

The previously mentioned retroviral expression vector pMV7 was utilized to introduce a cDNA encoding the beta1 isoform of PKC into FDC-P1 cells. FDC-P1 is a bone marrow-derived cell line which requires interleukin-3 (IL-3) for growth. In these studies, the hemopoietic cell line FDC-P1 was utilized in order to demonstrate the utility of the screening method even in cells which have very stringent growth requirements and would otherwise be very difficult to maintain in culture.

The following abbreviations are used herein: SDS, sodium dodecyl sulfate; EGTA, ethylene glycol bis (beta aminoethyl ether) N,N,N',N'-tetraacetic acid; EDTA, ethylene diamine tetraacetic acid; TPA, 12-0-tetradecanoyl phorbol-13-acetate (also known as PMA); CHO, Chinese hamster ovary cells; DEAE, diethyl aminoethyl.

Cell Culture

FDC-P1 cells were routinely maintained in Dulbecco's modified eagle's medium containing 10% iron-supplemented calf serum. We added 10% WEHI-3B cell-contained medium as a source of IL-3 and subcultured the cells twice weekly to give 2×10E5 cells/ml.

Isolation of cell lines stably overexpressing PKC

Subconfluent [PSI]-2 cells expressing a cDNA clone encoding the complete PKCbeta1 sequence (Housey et al., 1988) and containing the G418 resistance gene were irradiated with 3000 rad. These cells were cocultivated with FDC-P1 grown as described above, and 8 ug/ml of polybrene was added. After 48 hours, the FDC-P1 cells were pelleted, plated in 35mm petri dishes containing 0.3% agar, 10% calf serum, and 10% WEHI conditioned medium, and selected with 0.3 mg/ml of G418. After 10 days colonies were aspirated from the agar and grown in liquid medium.

RNA isolation and blot hybridization

Total RNA was extracted (Chomczynski, 1987) from FDC-P1 cells and run on a 1.5% agarose gel, blotted to nitrocellulose, and probed with the nick-translated EcoRl-Pstl fragment of the RP-58 cDNA encoding PKCbeta1 (Housey, 1988). In separate experiments nitrocellulose blots were probed with either the BamH1 fragment of the murine GM-CSF cDNA (Lee, 1985) or the XhoI fragment of the murine IL-3 gene (Yokota, 1984), clones donated by Dr. Lee and labelled by nick-translation to 1×10E8 cpm/ug. The labelled PstI fragment of tubulin was used to examine RNA loading.

Western blotting of PKC

FDC-P1 cells were placed directly into a buffer containing 1% SDS; 2 mM EGTA; 2nM EDTA; 20 mM Tris-HCl, pH 8.0, and 1% beta mercaptoethanol. The sample was boiled and pelleted for 30 min. at 20 degrees C at 200,000×g. Then 80 ug of supernatant protein was electrophoresed on a 10% SDS polyacrylamide gel, and the proteins were transferred to nitrocellulose. The blot was blocked with bovine serum albumen and was probed with an antibody made to a conserved region of PKC (LLNQEEGEYYNVPIPE) which recognizes all forms of the enzyme (Stabel, 1987). The PKC standard was purified from rat brain by previously published procedures (Kraft, 1988).

Stable Overproduction of PKCbeta1 in FDC-P1 Cells

In order to generate FDC-P1 cells which stably overproduced PKCbeta1, we cocultured FDC-P1 cells, which are dependent upon a source of IL-3 for continued growth, with [PSI]-2 cells which produce a retrovirus encoding the complete PKC beta1 cDNA clone in the pMV7 expression vector. After 48 hours of cocultivation, the FDC-P1 cells were plated in soft agar in medium containing G418 and IL-3, and after 10 days of selection several colonies were aspirated and grown in liquid culture.

Approximately 30 of these clones were screened by western blotting with a PKC antibody which recognizes all forms of PKC. A number of clones demonstrated elevated levels of PKC beta1 protein by Western blot analysis. Northern blot analyses were consistent with the western blot results and demonstrated that clones 40, 43, and 51 exhibited hybridizable bands to the EcoRl-Pstl fragment of the PKC-beta1 clone, whereas the parental cell line and clone 2 (which lacked any PKCbeta 1-specific mRNA), were negative. Furthermore, the total PKC activity in these cells was examined using histone IIIs as a phosphotransferase acceptor (Table 4). As expected, Clone 2 and the parental cell line had approximately the same PKC activity, whereas clones 40, 43, and 51 demonstrated approximately 20-fold increases in activity.

PKC Activators Induce Significant Morphologic Changes in FDC-P1 Cells That Stably Overproduce PKC We then tested the morphologic responsiveness of the FDC-P1 cells to activators of PKC induce profound morphologic changes in the FDC-P1 cells. Several cell lines were plated at 3×10E4 cells/ml and treated with 100 nM TPA. After 12 hours, representative fields were photographed. The PKC beta1 overproducing cells exhibited profound morphologic changes, including a generalized rounding up of the cells followed by the rapid formation of dense, cellular clumping. The latter clumps are easily visualized with standard cell stains such as Giemsa, and stain much darker than the corresponding control cells under these conditions.

Screening Assay to Detect Activators and Inhibitors of PKC

Thus, as with our previous findings for other cell lines such as NIH 3T3, Rat 6, and C3H 10T 1/2, this system also provides a rapid, powerful cell-based assay for the discovery and characterization of both activators and inhibitors of PKC as follows. Compounds could be rapidly screened for new activators of PKC by testing their ability to induce cellular clumping in the Test cells, while leaving the Control cells essentially unaffected. In addition, if one wanted to screen for PKC inhibitors, compounds could be rapidly screened for their ability to inhibit the effects of PKC by testing their ability to prevent cellular clumping induced by TPA in the Test cells, while again leaving the Control cells essentially unaffected. In this latter test, Control and Test cells would be incubated simultaneously with 100 nM TPA and the individual compounds to be tested. After 12 hours the Control and Test cells would be stained and scored for the inhibition of cellular clumping in the Test cells while leaving the Control cells unaffected.

EXAMPLE 5

In further studies designed to test the utility of this system with other proteins of interest (POI), we have utilized the human insulin receptor as a model POI. Cell lines which stably overproduce the insulin receptor were used to develop an assay system which is capable of detecting both agonists and antagonists of insulin action.

In the majority of vertebrates, insulin is the primary hormone involved in the homeostatic control of blood glucose levels. The many effects of insulin action on cells include stimulation of glucose, protein, and lipid metabolism as well as effects on RNA and DNA synthesis (Metcalf, 1985). These actions of insulin on cells begin at the molecular level through the binding of insulin to the insulin receptor. The insulin receptor is present on virtually all mammalian cells, but its number varies from as few as 40 to more than 200,000 receptors per cell (Kahn and White, 1988, and references therein). The insulin receptor is a heterotetrameric glycoprotein consistent of two alpha and two beta subunits. The alpha subunits, Mr=135,000, are located entirely extracellularly, whereas the beta subunits are transmembrane proteins which possess intrinsic tyrosine kinase activity. The alpha and beta subunits are attached by disulfide bonds on the extracellular side of the cell membrane. Both the alpha and the beta chains of the mature receptor molecule are derived from a single chain precursor polypeptide (the "proreceptor") which in turn is encoded by a single gene.

It is now known that the beta subunit of the insulin receptor is a protein tyrosine kinase which phosphorylates substrate proteins on tyrosine residues. This tyrosine kinase activity of the beta subunit is stimulated by the binding of insulin to the alpha subunit, and it has been shown that the tyrosine kinase activity of the beta subunit is essential for insulin action on target cells (Kahn and White, 1988, and references therein).

Generation of CHO Cell Lines Stably Overproducing the Human Insulin Receptor

In additional demonstrations of the utility of the method, we have employed Chinese Hamster Ovary (CHO) cell lines which stably overproduce the human insulin receptor (HIR) (White et al., 1988). These cell lines were generated using approaches analogous to those previously described for the PKC-overproducing cell lines. However, in these HIR studies we utilized a different expression vector, distinct cell lines, and an alternative method of gene transfer (direct transfection as opposed to virus-mediated transduction as used in the PKC experiments previously described). Briefly, CHO cells were co-transfected with the transfer vector pSVEneo (containing the neomycin resistance gene) and the expression vector pCVSVHIRc as previously described (White et al., 1988). After twenty four hours, the transfected cells were placed into 800 ug/ml G418 to select resistant cells. Approximately two weeks later, G418-resistant clones were isolated and subcloned. Clonal cell lines which express high levels of surface insulin receptors were selected by fluorescence-activated cell sorting. One such line (CHO/HIRC), which stably overproduced approximately 80,000 insulin receptors per CHO cell, was utilized in these experiments. A control CHO cell line (CHO/NEO), harboring only the pSVEneo transfer vector, were generated in analogous fashion. Detailed preliminary characterizations of this cell line have been described (White et al., 1988).

Morphologic and Growth Control Effects of Insulin Treatment on CHO Cells Stably Overproducing the Human Insulin Receptor We then tested the ability of the CHO/HIRC and CHO/NEO cells to respond to the following insulin treatment protocol. Control cells, hereinafter termed CHO/NEO (which harbor pSVEneo alone), and the Test cells, termed CHO/HIRC (which stably overproduced about 80,000 insulin receptors per cell), were incubated in the presence and absence of insulin. Control (CHO/NEO) and Test (CHO/HIRC) cell lines were exposed to 400 nM of insulin and the resultant morphologic changes were observed and photographed using a Bausch and Lomb BL-200 phase-contrast microscope with a Nikon FM-200 camera attached.

After 18 hours the test cells began to exhibit profound morphologic changes, including increased refractility, cellular rounding, and decreased adherence to the culture plate (anchorage dependence). These effects were further pronounced at 24 hours after exposure. Indeed, by 48 hours after treatment, virtually all of the test cells had completely detached from the plate, whereas the control cells were still largely intact. If the test cells were transferred to new plates in medium lacking high levels of insulin, however, they were completely viable and would attach to the plate and continue to grow normally. Thus, although insulin treatment could rapidly induce the anchorage independent phenotype, the cells remained completely viable for future growth if insulin was subsequently removed from their growth medium.

Screening Assay to Detect Activators and Inhibitors of the Insulin Receptor

Thus, in yet another demonstration of the utility of our method, the system described above provides a rapid and powerful screening method for the discovery and characterization of insulin agonists and antagonists as follows.

Compounds may be screened by testing their ability to preferentially induce anchorage-independent growth in the Test cells relative to the Control cells. Each compound would be applied to both the Control and the Test cells growing in multi-well plates, and 48 hours later the wells would be stained with a simple dye such as Giemsa (Housey et al., 1988 and references therein).

Whereas the Control CHO/NEO cells would consistently remain attached to the plate and stain strongly with Giemsa, the Test CHO/HIRC cells would be induced to detach from the plate by compounds which mimic the effects of insulin and therefore would no longer be stained by Giemsa. A standard microtitre well plate-reader (such as those produced by SLT America, Inc.) could easily read the absorbance of each well due to the staining procedure(s) used.

Thus, in this manner thousands of compounds could be screened for their ability to mimic the effects of insulin. Such agents are, of course, insulin agonists. However, as with the methods described above for PKC, the method could also be utilized for the discovery of insulin antagonists by simply treating the Control and Test Cells with potential antagonist compounds in the presence of insulin.

By this latter approach, compounds capable of inhibiting the effects of insulin action would prevent the induction of anchorage independence in the CHO/HIRC cells, whereas compounds with no effect would be unable to prevent the induction of anchorage-independent growth in the Test Cells. Most importantly, this insulin receptor assay system demonstrates yet another direct application of the utility of stable overproduction of a protein-of-interest (POI) for the development of powerful assay systems capable of detecting activators or inhibitors of any POI.

Julius, et al., Science, 244: 1057-62 (Jun. 2, 1989) reports the production of a cell line which overproduces the serotonin receptor 5HTlc by cloning its cDNA into the expression vector pMV7. The transformed cell lines exhibited a change in morphology, specifically, the formation of foci. Mesulergine, a serotonin antagonist, completely blocked the formation of foci. This paper was published after the filing date of the parent application, Feb. 10, 1988, and is therefore cited merely to further demonstrate the broad applicability of the screening method described herein.

Further Modifications

Use of any expression vector capable of stably overexpressing a given gene in a recipient cell could be used with success in the procedures described herein. The retroviral vector which I used here was particularly well suited to the problem since I had designed it specifically for these purposes. However, other similar vector systems would work. Also, one could do co-transfection of an experimental gene inserted in one plasmid vector along with a second plasmid containing the selectable marker gene (rather than having both the experimental gene and the selectable marker gene on the same plasmid vector). This is more difficult and less efficient than using the pMV7 vector, but it would work to some extent.

Any growth medium, in addition to soft agar or methocel, which tends to prohibit the growth of normal, non-transformed cells, could also be used.

A culture of E. coli DH1 bearing the plasmid denoted pMV7-RP58 (pMV7-PKC beta1), was deposited under the Budapest Treaty with the American Type Culture Collection on Feb. 11, 1988, ATCC No. 67654. The deposit of this plasmid is not to be construed as an admission that the deposit is required for enablement or that the disclosure is limited to the deposited vector or gene.

TABLE 1(a)

PKC Activity and Phorbol Ester Binding in Rat 6 Cells Infected with pMV7 or pMV7-PKCbeta1 Constructs

| Cell Line | PKC Activity Specific Activity (pmol/min/mg prot) | Fold Increase Relative to Control | 3H-PDBU Binding (pmol/$10^6$ cells) |
| --- | --- | --- | --- |
| R6-C1 | 100 | — | 1.6 |
| R6-C2 | 85 | — | 1.3 |
| R6-C3 | 150 | — | 1.5 |
| mean + s.d. | 100 + 34 | 1 | |
| R6-PKC1 | 2480 | 23 | 12.7 |
| R6-PKC2 | 85 | 1 | ND |
| R6-PKC3 | 5840 | 53 | 9.9 |
| R6-PKC4 | 190 | 2 | 0.7 |
| RE-PKC5 | 2200 | 20 | 5.8 |
| R6-PKC6 | 4600 | 42 | 7.1 |
| R6-PKC7 | 2150 | 20 | ND |
| R6-PKC8 | 3280 | 30 | ND |

TABLE 1(a)-continued

PKC Activity and Phorbol Ester Binding in Rat 6 Cells
Infected with pMV7 or pMV7-PKCbetal Constructs

| Cell Line | PKC Activity Specific Activity (pmol/min/mg prot) | Fold Increase Relative to Control | 3H-PDBU Binding (pmol/$10^6$ cells) |
|---|---|---|---|
| R6-PKC9 | 4990 | 45 | ND |
| R6-PKC10 | 5050 | 46 | ND |

TABLE 1(b)

PKC Activity in NIH-3T3 Cell Lines
Infected with pMV7 or pMV7-PKCbetal Constructs

| NIH-3T3 Cell lines (Controls) | PKC Specific Activity (pmol/min/mg prot) | Fold Increase Relative to Control |
|---|---|---|
| 3T3-C1 | 110 | — |
| 3T3-C2 | 150 | — |
| 3T3-C3 | 90 | — |
| mean +/- s.d. (control lines) | 115 +/- 30 | |
| NIH-3T3 PKC-Overproducing Cell Lines | | |
| 3T3-PKC1 | 2570 | 22 |
| 3T3-PKC2 | 3640 | 32 |
| 3T3-PKC3 | 1960 | 17 |
| 3T3-PKC4 | 1240 | 11 |
| 3T3-PKC5 | 4190 | 36 |
| 3T3-PKC6 | 2110 | 18 |
| 3T3-PKC7 | 5050 | 44 |

TABLE 1(c)

PKC Activity in C3H-10T1/2 Cell Lines
Infected with pMV7 or pMV7-PKCbetal Constructs

| C3H-10T1/2 Cell lines (Controls) | PKC Specific Activity (pmol/min/mg prot) | Fold Increase Relative to Control |
|---|---|---|
| C3H-C1 | 115 | — |
| C3H-C2 | 155 | — |
| C3H-C3 | 130 | — |
| C3H-C4 | 185 | — |
| mean +/- s.d. | 145 +/- 30 | |
| C3H-10T1/2 PKC-Overproducing Cell Lines | | |
| C3H-PKC1 | 2340 | 16 |
| C3H-PKC2 | 5010 | 35 |
| C3H-PKC3 | 950 | 7 |
| C3H-PKC4 | 1360 | 9 |
| C3H-PKC5 | 4340 | 30 |
| C3H-PKC6 | 7460 | 51 |

Legend to Table 1
Control cell lines were obtained by infecting rat-6-fibroblast, NIH-3T3 and C3H-10T1/2 cells with the pMV7 vector itself (lacking the PKC cDNA insert) whereas the PKC-overproducing cell lines were obtained from rat-6-fibroblast, NIH-3T3 and C3H-10T1/2 cells infected with the pMV7-PKCbeta construct, as described above. Total PKC activity was partially purified from each of the cell lines and assayed in the presence of 1 mM Ca2+ and 80 ug/ml phosphatidylserine, using the synthetic peptide R—K—R—T—L—R—R—L as substrate. Specific activity is reported as the amount of incorporation of 32P into the synthetic peptide substrate per milligram of protein per minute. All assays were done in duplicate and varied by less than 10%.

TABLE 2

GROWTH PROPERTIES OF RAT 6 CELL LINES OVERPRODUCING
PKC AND THEIR RESPONSES TO TREATMENT

Growth in Culture

| Cell Line | TPA Add | Monolayer Doubling Time (hrs) | Saturat. Density (× $10^6$) | Agar Effic. (%) | Colony Size (mm) |
|---|---|---|---|---|---|
| R6C1 | − | 26.4 | 3.4 | 0 | — |
| (control) | + | 24.6 | 4.2 | 0 | — |
| R6-PKC3 | − | 24.2 | 5.7 | 25.1 | 0.10–0.15 |
| (test) | + | 21.5 | 10.0 | 29.7 | 0.15–0.35 |
| R6-PKC5 | − | 24.9 | 4.8 | 17.3 | 0.05–0.10 |
| (test) | + | 22.9 | 7.0 | 34.7 | 0.10–0.15 |

Table 2.
The cells were grown as described above. The "doubling times" relate to the initial exponential phase of cell growth and the "saturation density" represents the number of cells per 6 cm plate on day 11. The data are taken from the experiment shown in FIG. 3.

TABLE 3

Inhibition of Growth in Agar of PKC-Overproducing
Cell Lines Using Various Inhibitors

| Inhibitor | Cell Line | Conc. Inhibitor (uM) | Effic. of Growth in Agar (%) |
|---|---|---|---|
| H-7 | R6-PKC3 | 0 | 27 |
| H-7 | R6-PKC3 | 2 | 25 |
| H-7 | R6-PKC3 | 5 | 22 |
| H-7 | R6-PKC3 | 10 | 17 |
| H-7 | R6-PKC3 | 50 | 4 |
| H-7 | R6-PKC3 | 100 | 0 |
| H-7 | R6-PKC5 | 0 | 20 |
| H-7 | R6-PKC5 | 2 | 21 |
| H-7 | R6-PKC5 | 5 | 16 |
| H-7 | R6-PKC5 | 10 | 4 |
| H-7 | R6-PKC5 | 50 | 1 |
| H-7 | R6-PKC5 | 100 | 0 |
| Tamoxifen | R6-PXC3 | 0 | 25 |
| Tamoxifen | R6-PKC3 | 5 | 27 |
| Tamoxifen | R6-PKC3 | 20 | 22 |
| Tamoxifen | R6-PKC3 | 50 | 15 |
| Tamoxifen | R6-PKC3 | 100 | 6 |
| Tamoxifen | R6-PKC3 | 200 | 0 |
| Tamoxifen | R6-PKC5 | 0 | 19 |
| Tamoxifen | R6-PKC5 | 5 | 19 |
| Tamoxifen | R6-PKC5 | 20 | 17 |
| Tamoxifen | R6-PKC5 | 50 | 8 |
| Tamoxifen | R6-PKC5 | 100 | 0 |
| Tamoxifen | R6-PKC5 | 200 | 0 |
| Staurosporine | R6-PKC3 | 0 | 29 |
| Staurosporine | R6-PKC3 | 0.001 | 29 |
| Staurosporine | R6-PKC3 | 0.005 | 26 |
| Staurosporine | R6-PKC3 | 0.010 | 15 |
| Staurosporine | R6-PKC3 | 0.050 | 7 |
| Staurosporine | R6-PKC3 | 0.250 | 0 |
| Staurosporine | R6-PKC5 | 0 | 22 |
| Staurosporine | R6-PKC5 | 0.001 | 21 |
| Staurosporine | R6-PKC5 | 0.005 | 17 |
| Staurosporine | R6-PKC5 | 0.010 | 10 |
| Staurosporine | R6-PKC5 | 0.050 | 2 |
| Staurosporine | R6-PKC5 | 0.250 | 0 |

TABLE 4

PKC Activity in FDC-P1 Cells Transfected with a Retrovirus Encoding PKCbetal

| Cell Line | PKC Activity (pmol/min/ug prot) | Fold Increase Relative to Parental Cell Line |
|---|---|---|
| Parental Control | 78 | 1 |
| FDC-P1 clone 2 | 64 | 1 |
| FDC-P1 clone 4 | 1873 | 24 |
| FDC-P1 clone 43 | 1558 | 20 |
| FDC-P1 clone 51 | 1135 | 15 |

Approximately 3×10E7 cells in the logarithmic phase of growth were homogenized, supernatants places over a DEAE-cellulose, and eluates assayed as previously described (Kraft, 1983).

References

Ashendel, C. The Phorbol Ester Receptor: a phospholipid-regulated protein kinase. (1984) Biochim. Biophys. Acta 822, 219–242.

Bollag, G. E., Roth, R. A., Beaudoin, J., Mochly-Rosen, D., Koshland, D. E. Jr. (1986) Protein kinase C directly phosphorylates the insulin receptor in vitro and reduces its protein-tyrosine kinase activity. Proc. Natl. Acad Sci. USA 83, pp 5822–4.

Boreiko, C., Mondal, S., Narayan, S., and Heidelberger, C. (1980) Effect of 12–0-Tetradecanoylphorbol-13-acetate on the Morphology and Growth of C3H/10/2 Mouse Embryo Cells. Cancer Res. 40, 4709–4716.

Bradford, M. M. (1976) A rapid and sensitive method for the quantitation of microgram quantities of protein utilizing the principle of protein-dye binding. Anal. Biochem. 72, 248–254.

Brandt, S. J., Niedel, J. E., Bell, R. M., Young, W. S. (1987) Distinct patterns of expression of different protein kinase C mRNAs in rat tissues. Cell 49, pp 57–63.

Catino, J. J., Francher, D. M., Edinger, K. J., and Stringfellow, D. A. (1985) A microtitre cytotoxicity assay useful for the discovery of fermentation-derived antitumor agents. Cancer Chemother. Pharmacol. 15, 240–243.

Chomczynski, P., Sacchi, N. (1987), Anal. Biochem., 162: 156–159.

Coussens, L., Parker, P. J., Rhee, L., Yang-Feng, T. L., Chen, E., Waterfield, M. D., Francke, U., & Ullrich, A. (1986) Multiple, distinct forms of bovine and human protein kinase C suggest diversity in cellular signalling pathways. Science 233, 859–866.

Dailey, L., and Basilico, C. (1985). Sequences in the polyomavirus DNA regulatory region involved in viral DNA replication and early gene expression. J. Virol. 54, 739–749.

Daley, G. Q., McLaughlin, J., Witte, 0. N., Baltimore, D. The CML-Specific P210 bcr/abl Protein, Unlike v-abl, Does Not Transform NIH/3T3 Fibroblasts Science 237, pp 532–535.

Davis, R. J., and Czech, M. P. (1985) Platelet-derived growth factor mimics phorbol diester action on epidermal growth factor receptor phosphorylation at threonine 654. Proc. Natl. Acad. Sci. 82, 4080–4084.

Freeman, A. E., Price, P. J., Igel, H. J., Young, J. C., Maryak, J. M. Huebner, R. J. (1970) Morphological transformation of rat embryo cells induced sa dimethylnitrosamine and murine leukemia viruses. J. Natl. Cancer Inst. 44, pp 65–78.

Freedman, V. H. and Shin, S. (1974) Cellular Tumorigenicity in nude Mice: Correlation with Cell Growth in Semi-Solid Medium. Cell 3, 355–359.

Graham, F. L., and van der Eb, A. J. (1973) A new technique for the assay of infectivity of human adenovirus DNA. Virology 52, 456–467.

Gould, K. L., Woodgett, J. R., Cooper, J. A., Buss, J. E., Shalloway, D., Hunter, T. (1985) Protein Kinase C Phosphorylates pp60src at a novel site. Cell 42, pp 849–857.

Horowitz, A. D., Greenebaum, E. and Weinstein, I. B. (1981) Identification of receptors for phorbol ester tumor promoters in intact mammalian cells and of an inhibitor of receptor binding in biologic fluids. Proc. Natl. Acad. Sci. U.S.A. 78, pp 2315–2319.

Housey. G. M., O'Brian, C. A., Johnson, M. D., Kirschmeier, P., and Weinstein, I. B. (1987) Isolation of cDNA clones encoding protein kinase C: Evidence for a protein kinase C-related gene family. Proc. Natl. Acad. Sci. U.S.A. 84, pp 1065–1069.

Housey, G. M., Kirschmeier, P., Garte, S. J., Burns, F., Troll, W., & Weinstein, I. B. (1985) Expression of long terminal repeat (LTR) sequences in carcinogen-induced murine skin carcinomas. Biochem. Biophys. Res. Commun. 127, 391–398.

Hsiao, W.-L. W., T. Wu, Wainstein, I. B., (198C) Oncogene-Induced Transformation of a Rat Embryo Fibroblast Cell Line is Enhanced by Tumor Promoters. Mol. Cell. Biol. 6, pp 1943–1950.

Hunter, T., Ling, N., Cooper, J. A. (1984) Protein kinase C phosphorylation of the EGF receptor at a threonine residue close to the cytoplasmic face of the plasma membrane. Nature 311, 480–3.

Huang, K. P., Nakabayashi, H., Huang, F. L. (1986) Isozymic forms of rat brain Ca2+-activated, phospholipid-dependent protein kinase. Proc. Natl. Acad. Sci. 83, 8535–8539.

Housey, G. M., Johnson, M. D., Hsiao, W. L., O'Brian, C. A., Murphy, J. P., Kirschmeier, P. and Weinstein, I. B., (1988), Cell, 52: 343–54.

Jaken, S. and Kiley, S. (1987) Purification and characterization of three types of protein kinase C from rabbit brain cytosol. Proc. Natl. Acad. Sci. U.S.A. 84, pp 4418–4422.

Jeng, A. Y., Srivastava, S. K., Lacal, J. C., Blumberg, P. M. (1987) Phosphorylation of ras oncogene product by protein kinase C. Biochem. Biophys. Res. Commun. 145, pp 782–8.

Johnson, M. D., Housey, G. M., Kirschmeier, P., and Weinstein, I. B. (1987) Molecular Cloning of Gene Sequences Regulated by Tumor Promoters Through Protein Kinase C. Mol. Cell Biol. 7, 2821–2829.

Kahn, C. R., White, M. F. (1988), The Insulin Receptor and the Molecular Mechanism of Insulin Action, J. Clin. Invest., 82: 1151–56.

Kajikawa, N., Kishimoto, A., Shiota, M., & Nishizuka, Y. (1983) Ca2+-dependent neutral protease and proteolytic activation of Ca2+-activated, phospholipid-dependent protein kinase. Methods. Enzymol. 102, 279–290.

Kawamoto, S. and Hidaka, H. (1984) 1-(5-Isoquinolinesulfonyl) -2-methyl-piperazine (H-7) is a selective inhibitor of protein kinase C in rabbit platelets. Biochem. Biophys. Res. Commun. 125, 258.

Kikkawa, U., Takai, Y., Minakuchi, R., Inohara, S., and Nishizuka, Y. (1982) Calcium-activated, phospholipid-dependent protein kinase from rat brain. Subcellular distribution, purification, and properties. J. Biol. Chem. 257, 13341–13348.

Kirschmeier, P. T., Housey, G. M., Johnson, M. D., Perkins, A. S., and Weinstein, I. B. (1988) Construction and Characterization of a Retroviral Vector Demonstrating Efficient Expression of Cloned cDNA Sequences. DNA, in press.

Knopf, J. L., Lee, M-H, Sultzman, L. A., Kriz, R. W., Loomis, C. R., Hewick, R. M. & Bell, R. (1986) Cloning and expression of multiple protein kinase C cDNAs. Cell 46, 491–502.

Kraft, A. S., Reeves, J. A. and Ashendel, C. L. (1988), J. Biol. Chem., 263: 8437–42.

Kraft and Anderson, W. B. (1983), J. Biol. Chem., 258: 9178–9183.

Laemmli, U. K. (1970) Cleavage of structural proteins during the assembly of the head of bacteriophage T4. Nature 227, 680–685.

Leach, K. L., James, M. L., & Blumberg, P. M., (1983) Characterization of a specific phorbol ester aporeceptor in mouse brain cytosol. Proc. Natl. Acad. Sci. U.S.A. 80, 4208–4212.

Lee, F., Yokota, T., Otsuka, T., Gemmell, L., Larson, N., Luh, J., Arai, K-I., and Rennick, D. (1985), Proc. Nat. Acad. Sci. U.S.A., 82: 4360–64.

Lusky, M., and Botchan, M. (1981). Inhibition of SV40 replication in simian cells by specific pBR322 DNA sequences. Nature 293, 74–81.

Maddon, P. J., Dalgleish, A. G., McDougal, J. S., Clapham, P. R., Weiss, R. A., Axel, R. (1986) The T4 Gene Encodes the AIDS Virus Receptor and Is Expressed in the Immune System and the Brain. Cell 47, pp 333–348.

Makowske, M., Birnbaum, M. J., Ballester, R., Rosen, O. M. (1986) A cDNA encoding PKC identifies two species of mRNA in brain and GH3 cells. J. Biol. Chem. 261, pp 3389–13392.

Maniatis, T., Fritsch, E. F., & Sambrook, J. eds. (1983) in Molecular Cloning : A Laboratory Manual (Cold Spring Harbor Laboratory, Cold Spring Harbor, N.Y.)

Mann, R., Mulligan, R. C., and Baltimore, D. (1983) Construction of a retrovirus packaging mutant and its use to produce helper-free defective retrovirus. Cell 33, 153–159.

Nishizuka, Y. (1986) Studies and Perspectives of Protein Kinase C. Science 233, 305–312. Nishizuka, Y. (1984) The Role of Protein Kinase C in Cell Surface Transduction and Tumour Promotion. Nature (London) 308, 693–698.

Metcalf, D., (1985) Science, 229, 16–22.

O'Brian, C. A., Lawrence, D. S., Kaiser, E. T., & Weinstein, I. B. (1984) Protein kinase C phosphorylates the synthetic peptide Arg-Arg-Lys-Ala-Ser-Gly-Pro-Pro-Val in the presence of phospholipid plus either Ca2+ or a phorbol ester tumor promoter. Biochem. Biophys. Res. Commun. 124, 296–302.

O'Brian, C., Arcoleo, J., Housey, G. M., & Weinstein, I. B. (1985) in Cancer Cells 3, eds. Feramisco, J., Ozanne, B. & Stiles, C. (Cold Spring Harbor Laboratory, Cold Spring Harbor, N.Y.) 359–363.

O'Brian, C. A., Liskamp, R. M., Solomon, D. H. and Weinstein, I. B. (1985) Inhibition of Protein Kinase C by Tamoxifen. Cancer Res. 45, 2462–2465.

Ono, Y., Kurokawa, T., Fujii, T., Kawahara, K., Igarashi, K., Kikkawa, U., Ogita, K., Nishizuka, Y. (1986) Two types of complementary DNAs of rat brain protein kinase C. FEBS 206, 347–52.

Ono, Y., Kikkawa, U., Ogita, K., Tomoko, F., Kurokawa, T., Asaoka, Y., Sekiguchi, K., Ase, K., Igarashi, K., Nishizuka, Y. (1987) Expression and Properties of Two Types of Protein Kinase C: Alternative splicing from a Single Gene. Science 236, pp 1116–1120.

Ohno, S., Kawasaki, H., Imajoh, S., Suzuki, K., Inagaki, M., Yokohura, H., Sakoh, T., Hidaka, H. (1987) Tissue-specific expression of three distinct types of rabbit protein kinase C. Nature (London) 325, pp 161–6.

Parker, P. J., Coussens, L., Totty, N., Rhee, L., Young, S., Chen, E., Stabel, S., Waterfield, M. D., & Ullrich, A. (1986) The complete primary structure of protein kinase C--the major phorbol ester receptor. Science 233, 853–858.

Perkins, A. S., Kirschmeier, P. T., Gattoni-Celli, S., and Weinstein, I. B. (1983). Design of a retrovirus-derived vector for expression and transduction of exogenous genes in mammalian cells. Mol. Cell. Biol. 3, 1123–1132.

Pontremoli, S., Melloni, E., Michetti, M., Sparatore, B., Salamino, F., Sacco, O., and Horecker, B. L. (1987) Phosphorylation and proteolytic modification of specific cytoskeletal proteins in human neutrophils stimulated by phorbol-12-myristate 13-acetate. Proc. Natl. Acad. Sci. 84, 3604–3608.

Sibley, D. R., Benovic, J. L., Caron, M. G., Lefkowitz, R. J. (1987) Regulation of transmembrane signalling by receptor phosphorylation. Cell 48, 913–922.

Stabel, S., Rodriguez-Pena, A., Young S., Rozengurt E., and Parker, P. J. (1987), J. Cell Physiol., 130: 111–117.

Uehara, Y., Hori, M., Takeuchi, T., Umezawa, H. (1985) screening of Agents Which Convert 'Transformed Morphology' of Rous Sarcoma Virus-Infected Rat Kidney Cells to 'Normal Morphology': Identification of an Active Agent as Herbimycin and its Inhibition of Intracellular src Kinase. Jpn. J. Cancer Res. 76, 672–675.

Ullrich, A., Coussens, L., Hayflick, J. S., Dull, T. J., Gray, A., Tam, A. W., Lee, J., Yarden, Y., Libermann, T. A., Schlessinger, J., Downward, J., Mayes, E. L. V., Whittle, N., Waterfield, M. D., and Seeburg, P. H. Human epidermal growth factor receptor cDNA sequence and aberrant expression of the amplified gene in A431 epidermoid carcinoma cells. Nature 309, 418–425.

Walton, G. M., Bertics, P. J., Hudson, L. G., Vedvick, T. S., Gill, G. N. (1987) A Three-Step Purification Procedure for Protein Kinase C: Characterization of the Purified Enzyme. Anal. Biochem. 161, 425–437.

Weinstein, I. B., (1987) Growth Factors, Oncogenes, and Multistage Carcinogenesis. J. Cell. Biochem. 33, pp 213–224.

White, M. F., Livingston, J. N., Backer, J. M., Lauris, V., Dull, T. J., Ullrich, A., Kahn, C. R., Mutation of the Insulin Receptor at Tyrosine 960 Inhibits Signal Transmission but Does Not Affect its Tyrosine Kinase Activity (1988), Cell, 54: 641–649.

Wigler, M., Silverstien, S., Lee, L.-S., Pellicer, A., Cheng, Y.-C, and Axel, R. (1977). Transfer of purified herpes virus thymidine kinase gene to cultured mouse cells. Cell 11, 223–232.

Woodgett, J. R., Gould, K. L., and Hunter, T. (1986) Substrate specificity of protein kinase C. Use of synthetic peptides corresponding to physiological sites as probes for substrate recognition requirements. Eur. J. Biochem. 161 177–184.

Yokota, T., Lee, F., Rennick, D., Hall, C., Aria, N., Mosmann, T., Nabel, G., Cantor, H., and Arai, K-I., (1984), Proc. Nat. Acad. Sci. USA 81: 1070–74.

Young, S., Parker, P. J., Ullrich, A., and Stabel, S. (1987) Down-regulation of protein kinase C is due to an increased rate of degradation. Biochem. J. 244, 775–779.

Von Hoff, D. D., Forseth, B., and Warfel, L. E. (1985) se of a Radiometric System to Screen for Antineoplastic Agents: Correlation with a Human Tumor Cloning System. Cancer Res. 45, 4032–4036.

I claim:

1. A test cell in which there is present in the cell a target protein, wherein the presence of the target protein induces a change in a selected phenotypic characteristic of the test cell, other than the level of the target protein in the test cell, per se, wherein the change in the selected phenotypic characteristic is comparatively greater in the test cell than in a control cell, and wherein the change in the selected phenotypic characteristic has been found to be responsive to treatment with a test substance that is capable of inhibiting or activating a biochemical function of the target protein, by a method comprising the steps of:

a) providing a test cell in which a target protein is present at a higher level relative to a control cell which produces the protein at a lower level or essentially does not produce the protein;

b) treating the test cell of step (a) containing the target protein of step (a) with a test substance; and c) examining the treated test cell of step (b) to determine whether an selected phenotypic characteristic that is responsive to inhibition or activation of the target protein of step (a) has been altered by treatment with the test substance of step (b).

* * * * *